United States Patent
Larson et al.

(10) Patent No.: US 7,153,561 B2
(45) Date of Patent: Dec. 26, 2006

(54) ABSORBENT ARTICLE WITH GRAPHIC DESIGN THEREON

(75) Inventors: Todd Christopher Larson, Appleton, WI (US); Mark M. Mleziva, Appleton, WI (US); Michael Donald Sperl, Waupaca, WI (US); Paula Mary Sosalla, Appleton, WI (US)

(73) Assignee: Kimberly-Clark Wordwide, Inc., Neenah, WI (US)

( * ) Notice: Subject to any disclaimer, the term of this patent is extended or adjusted under 35 U.S.C. 154(b) by 342 days.

(21) Appl. No.: 10/618,030

(22) Filed: Jul. 11, 2003

(65) Prior Publication Data

US 2005/0008827 A1 Jan. 13, 2005

(51) Int. Cl.
*B32B 3/00* (2006.01)

(52) U.S. Cl. .................. 428/195.1; 428/201; 428/204; 428/207; 428/690; 283/85; 283/92; 283/93

(58) Field of Classification Search ............. 428/195.1, 428/690, 201, 204, 207; 427/157; 604/361, 604/358; 283/85, 92, 93
See application file for complete search history.

(56) References Cited

U.S. PATENT DOCUMENTS

| | | | |
|---|---|---|---|
| 2,277,169 A | 3/1942 | Switzer et al. | |
| 2,536,631 A | 1/1951 | Ely | |
| 2,629,956 A | 3/1953 | Switzer | |
| 2,650,169 A | 8/1953 | Goldstein | |
| 3,591,445 A | 7/1971 | Schonberg et al. | |
| 3,738,299 A | 6/1973 | Packler et al. | |
| 4,244,369 A | 1/1981 | McAvinn et al. | |
| 4,626,252 A | 12/1986 | Nishizawa et al. | |
| 4,663,220 A | 5/1987 | Wisneski et al. | |
| 4,704,116 A | 11/1987 | Enloe | |
| 4,896,600 A | 1/1990 | Rogge et al. | |
| 4,909,879 A | 3/1990 | Ball | |
| 4,940,464 A | 7/1990 | Van Gompel et al. | |
| 5,046,272 A | 9/1991 | Vogt et al. | |
| 5,104,116 A | 4/1992 | Pohjola | |
| 5,224,405 A | 7/1993 | Pohjola | |
| 5,226,992 A | 7/1993 | Morman | |
| 5,270,100 A | 12/1993 | Giglio | |

(Continued)

FOREIGN PATENT DOCUMENTS

EP 0 217 032 A2 4/1987

(Continued)

OTHER PUBLICATIONS

International Search Report from PCT/US2004/011053 dated Oct. 27, 2004.

*Primary Examiner*—Marie Yamnitzky
*Assistant Examiner*—Camie S. Thompson
(74) *Attorney, Agent, or Firm*—Senniger Powers

(57) ABSTRACT

In a substrate having a graphic and a method for applying the graphic thereto, a non-phosphorescent material is applied to the substrate to define a non-phosphorescent region of the graphic and a phosphorescent material is applied to the substrate to define a phosphorescent region of the graphic. At least a portion of the non-phosphorescent region and at least a portion of the phosphorescent region are in overlapping relationship with each other so as to define an overlapping region of the graphic. When the overlapping region is exposed to light sufficient to cause phosphorescence of the phosphorescent region the at least a portion of the phosphorescent region phosphoresces to render the overlapping region visible in the absence of light. In another embodiment, the graphic has a non-photoluminescent region in overlapping relationship with a photoluminescent region.

47 Claims, 14 Drawing Sheets

U.S. PATENT DOCUMENTS

| | | | |
|---|---|---|---|
| 5,279,859 | A | 1/1994 | May |
| 5,458,590 | A | 10/1995 | Schleinz et al. |
| 5,566,616 | A | 10/1996 | Schleinz et al. |
| 5,588,156 | A | 12/1996 | Panton, Jr. |
| 5,599,048 | A | 2/1997 | Schioler |
| 5,612,118 | A | 3/1997 | Schleinz et al. |
| 5,766,389 | A | 6/1998 | Brandon et al. |
| 5,858,515 | A | 1/1999 | Stokes et al. |
| 5,960,471 | A | 10/1999 | Burton |
| 5,965,242 | A | 10/1999 | Patton et al. |
| 6,066,774 | A | 5/2000 | Roe |
| 6,210,776 | B1 | 4/2001 | Hill |
| 6,279,161 | B1 | 8/2001 | Johnston |
| 6,501,002 | B1 | 12/2002 | Roe et al. |
| 6,645,190 | B1 | 11/2003 | Olson et al. |
| 6,683,228 | B1 | 1/2004 | Pacheco, Sr. |
| 2001/0047144 | A1 | 11/2001 | Tilotson et al. |
| 2001/0051177 | A1 | 12/2001 | Leutz et al. |
| 2003/0019374 | A1 | 1/2003 | Harte |
| 2003/0225386 | A1* | 12/2003 | Rodriguez ............. 604/385.03 |
| 2003/0229325 | A1 | 12/2003 | Belau et al. |
| 2004/0139881 | A1 | 7/2004 | Kaz et al. |
| 2005/0008830 | A1* | 1/2005 | Larson et al. ............. 428/195.1 |

FOREIGN PATENT DOCUMENTS

| | | |
|---|---|---|
| EP | 0 539 001 | 4/1993 |
| EP | 1 142 545 A2 | 10/2001 |
| KR | 10-2000-0024501 | 9/2000 |
| WO | WO 97/29319 A2 | 8/1997 |
| WO | WO 98/40223 | 9/1998 |
| WO | WO 99/32385 A1 | 7/1999 |
| WO | WO 00/27908 A2 | 5/2000 |
| WO | WO 00/37009 A2 | 6/2000 |
| WO | WO 00/65348 A2 | 11/2000 |
| WO | WO 01/56525 A1 | 8/2001 |
| WO | WO 01/64131 A2 | 9/2001 |
| WO | WO 01/88245 A2 | 11/2001 |
| WO | WO 02/22183 A2 | 3/2002 |

* cited by examiner

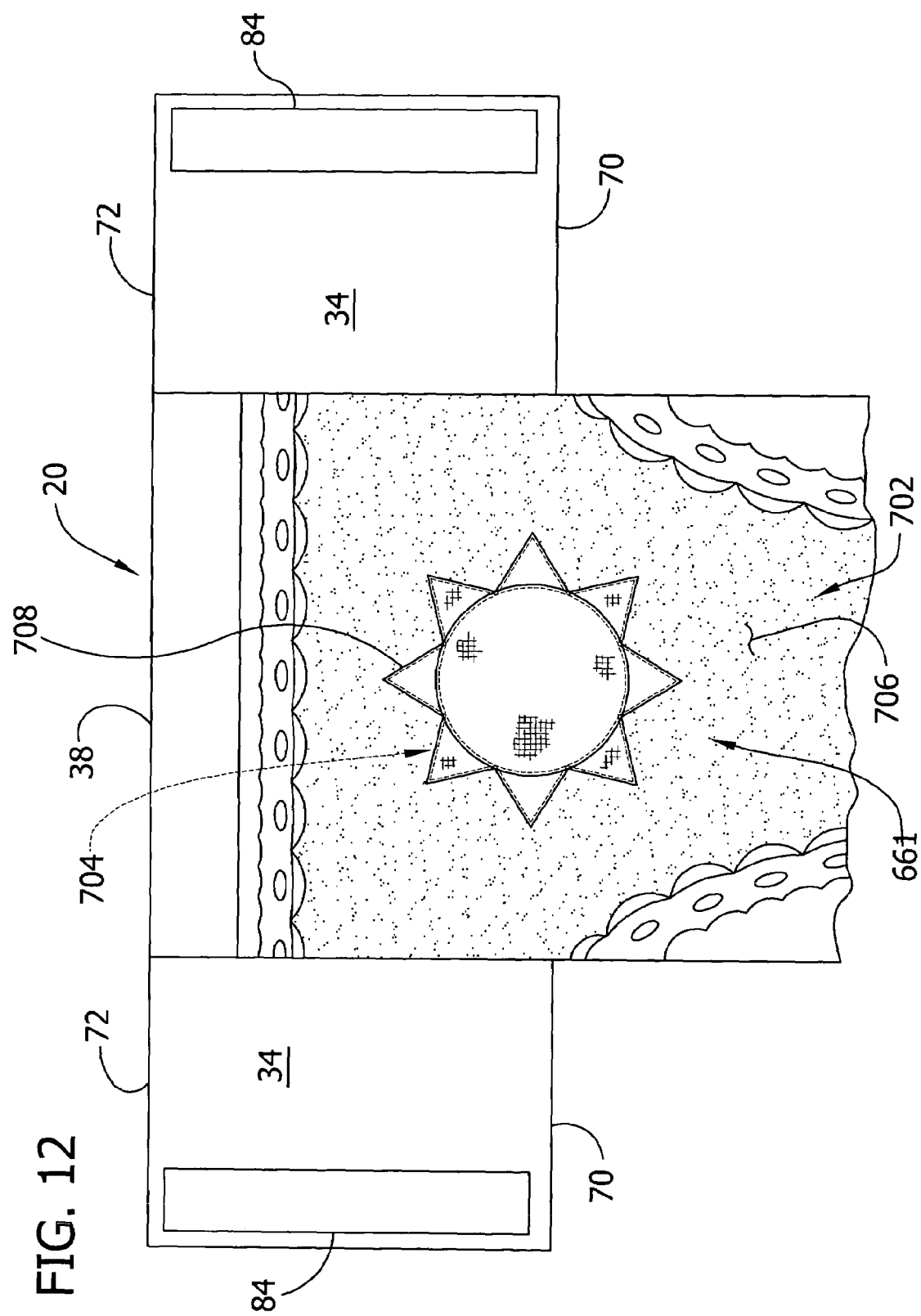

ABSORBENT ARTICLE WITH GRAPHIC DESIGN THEREON

BACKGROUND OF THE INVENTION

This invention relates generally to substrates used in making articles such as training pants, diapers, feminine hygiene products, incontinence garments and the like, and more particularly to such substrates having graphics thereon.

Personal wear articles find widespread use as personal care products including, without limitation, diapers, children's toilet training pants, adult incontinence garments, sanitary napkins and the like, as well as surgical bandages and sponges. Certain such articles are generally considered to be disposable in that they are usually intended to be discarded after a limited period of use, i.e., the articles are not intended to be laundered or otherwise restored for reuse. Disposable absorbent articles typically comprise an absorbent body disposed between a liner, which contacts the wearer's skin, and an outer cover, which inhibits liquid body waste absorbed by the absorbent body from leaking out of the article. The liner of the absorbent article is typically liquid permeable to permit liquid body waste to pass therethrough for absorption by the absorbent body.

Conventional absorbent articles also typically include some type of fastening system for securing the absorbent article in an assembled configuration and/or for fitting the article on the wearer, such as on the wearer's waist in the case of diapers and training pants. In many such applications, the fastening system is releasable and refastenable so that the article can be temporarily removed and then refastened to the wearer.

It is further known to apply a graphic, such as in the form of a character, object and/or alphanumeric (e.g., numbers, words, phrases, instructions, etc.) to personal wear articles to enhance the aesthetic or otherwise visual appearance or usefulness of the article. Graphics applied to such disposable articles may also provide visual assistance to the wearer or to a caregiver securing the article on the wearer. In some instances, the graphics may include a material or substance capable of being visible in low light conditions, including in the dark, to further enhance the appeal to the wearer or ease of use by the caregiver.

One common technique used to apply a graphic to a personal wear article, and more particularly to the outer cover thereof, is commonly known as flexographic printing and provides a cost effective, high speed, high quality printing technique for printing thin films or non-woven fibrous webs while maintaining the tactile softness of the film or web. Flexography involves the use of flexible, raised rubber or photopolymer plates to carry an image to a given substrate on which the graphic is applied. The flexible plates apply a typically low-viscosity ink directly onto the substrate.

Existing inks capable of glowing in the dark, and particularly those glow-in-the-dark inks which are suitable for flexographic printing, are not easily seen under normal light conditions (e.g., daytime light conditions). Thus, graphics or regions thereof formed by glow-in-the-dark inks are difficult to distinguish against white backgrounds during normal light conditions. To this end, a discrete glow-in-the-dark region of a graphic is typically surrounded by a visibly distinguishable region (e.g., distinguishable from the background) so that the glow-in-the-dark region can be discerned during normal light conditions. When printed on the inner film layer of a two-layer outer cover, existing glow-in-the-dark inks become even less visible once the non-woven outer layer of the outer cover is laminated over the inner film layer. Such an arrangement does not allow for printed graphics to be easily seen in both normal light conditions and in the dark.

SUMMARY OF THE INVENTION

In one embodiment, a substrate of the present invention has a a graphic generally comprising a non-phosphorescent material applied to the substrate to define a non-phosphorescent region of the graphic and a phosphorescent material applied to the substrate to define a phosphorescent region of the graphic. At least a portion of the non-phosphorescent region and at least a portion of the phosphorescent region are in overlapping relationship with each other so as to define an overlapping region of the graphic. When the overlapping region is exposed to light sufficient to cause phosphorescence of the phosphorescent region the at least a portion of the phosphorescent region phosphoresces to render the overlapping region visible in the absence of light.

In another embodiment, a substrate has a graphic thereon generally comprising a colored non-phosphorescent region and a phosphorescent region. At least a portion of the non-phosphorescent region and at least a portion of the phosphorescent region are in overlapping relationship with each other so as to define an overlapping region of the graphic. When the overlapping region is exposed to light sufficient to cause phosphorescence of the phosphorescent region the at least a portion of the phosphorescent region phosphoresces to render the overlapping region visible in the absence of light.

In general, a substrate according to another embodiment of the present invention has a graphic thereon comprising a non-photoluminescent material applied to the substrate to define a non-photoluminescent region of the graphic and a photoluminescent material applied to the substrate to define a photoluminescent region of the graphic. At least a portion of the non-photoluminescent region and at least a portion of the photoluminescent region are in overlapping relationship with each other so as to define an overlapping region of the graphic. When the overlapping region is exposed to light sufficient to cause luminescence of the photoluminescent region the at least a portion of the photoluminescent region luminesces.

In yet another embodiment, a substrate has a graphic thereon generally comprising a colored non-photoluminescent region and a photoluminescent region. At least a portion of the non-photoluminescent region and at least a portion of the photoluminescent region are in overlapping relationship with each other so as to define an overlapping region of the graphic wherein when the overlapping region is exposed to light sufficient to cause luminescence of the photoluminescent region said at least a portion of the photoluminescent region luminesces.

In one embodiment, an article of the present invention generally comprises a first substrate, a second substrate in overlaid relationship with the first substrate, and a graphic comprising a colored non-phosphorescent region and a phosphorescent region. At least a portion of the colored non-phosphorescent region and at least a portion of the phosphorescent region are in overlapping relationship with each other so as to define an overlapping region of the graphic. When the overlapping region is exposed to light sufficient to cause phosphorescence of the phosphorescent region, the at least a portion of the phosphorescent region phosphoresces to render the overlapping region visible in the absence of light. One of the first and second substrates has the colored non-phosphorescent region thereon and the other one of the first and second substrates has the phosphorescent region thereon.

In another embodiment, the article comprises a first substrate, a second substrate in overlaid relationship with the first substrate, and a graphic comprising a colored non-photoluminescent region and a photoluminescent region. At least a portion of the colored non-photoluminescent region and at least a portion of the photoluminescent region are in overlapping relationship with each other so as to define an overlapping region of the graphic. When the overlapping region is exposed to light sufficient to cause luminescence of the photoluminescent region, the portion of the photoluminescent region luminesces. One of the first and second substrates has the colored non-photoluminescent region thereon and the other one of the first and second substrates has the photoluminescent region thereon.

In general, one method of applying a graphic to a substrate generally comprises applying a non-phosphorescent material to the substrate to form a non-phosphorescent region of the graphic and applying a phosphorescent material to the substrate to form a phosphorescent region of the graphic. At at least a portion of the phosphorescent region and at least a portion of the non-phosphorescent region are in overlapping relationship with each other to form an overlapping region of the graphic wherein when the overlapping region is exposed to light sufficient to cause phosphorescence of the phosphorescent region said at least a portion of the phosphorescent region phosphoresces to render the overlapping region visible in the absence of light.

In another embodiment a method of applying a graphic to a substrate generally comprises applying a non-photoluminescent material to the substrate to form a non-photoluminescent region of the graphic and applying a photoluminescent material to the substrate to form a photoluminescent region of the graphic. At least a portion of the photoluminescent region and at least a portion of the colored non-photoluminescent region are in overlapping relationship with each other to form an overlapping region of the graphic wherein when the overlapping region is exposed to light sufficient to cause luminescence of the photoluminescent region the at least a portion of the photoluminescent region luminesces.

Definitions

Within the context of this specification, each term or phrase below will include the following meaning or meanings.

"Bonded" refers to the joining, adhering, connecting, attaching, or the like, of two elements. Two elements will be considered to be bonded together when they are bonded directly to one another or indirectly to one another, such as when each is directly bonded to intermediate elements.

"Elastic," "elasticized" and "elasticity" mean that property of a material or composite by virtue of which it tends to substantially recover its original size and shape after removal of a force causing a deformation.

"Elastomeric" refers to a material or composite which can be elongated by at least 25 percent of its relaxed length and which will recover, upon release of the applied force, at least 10 percent of its elongation. It is generally preferred that the elastomeric material or composite be capable of being elongated by at least 100 percent, more preferably by at least 300 percent, of its relaxed length and recover, upon release of an applied force, at least 50 percent of its elongation.

"Extensible" refers to a material or composite that is stretchable or capable of being elongated in at least one direction, but which may not have sufficient recovery to be considered elastic.

"Flexible" refers to materials which are compliant and which will readily conform to the general shape and contours of the wearer's body.

"Force" includes a physical influence exerted by one body on another which produces acceleration of bodies that are free to move and deformation of bodies that are not free to move. Force is expressed in grams per unit area.

"Hydrophilic" describes fibers or the surfaces of fibers which are wetted by the aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 Surface Force Analyzer System, or a substantially equivalent system. When measured with this system, fibers having contact angles less than 90 degrees are designated "wettable" or hydrophilic, while fibers having contact angles greater than 90 degrees are designated "nonwettable" or hydrophobic.

"Integral" is used to refer to various portions of a single unitary element rather than separate structures bonded to or placed with or placed near one another.

"Inward" and "outward" refer to positions relative to the center of an article, and particularly transversely and/or longitudinally closer to or away from the longitudinal and transverse center of the article.

"Layer" when used in the singular can have the dual meaning of a single element or a plurality of elements.

"Longitudinal" and "transverse" have their customary meaning, as indicated by the longitudinal and transverse axes depicted in FIGS. 2 and 3. The longitudinal axis lies in the plane of the article and is generally parallel to a vertical plane that bisects a standing wearer into left and right body halves when the article is worn. The transverse axis lies in the plane of the article generally perpendicular to the longitudinal axis. The article as illustrated is longer in the longitudinal direction than in the transverse direction.

"Nonwoven" and "nonwoven web" refer to materials and webs of material which are formed without the aid of a textile weaving or knitting process.

"Operatively joined," with reference to the attachment of an elastic member to another element, means that the elastic member when attached to or connected to the element, or treated with heat or chemicals, by stretching, or the like, gives the element elastic properties; and with reference to the attachment of a non-elastic member to another element, means that the member and element can be attached in any suitable manner that permits or allows them to perform the intended or described function of the joinder. The joining, attaching, connecting or the like can be either direct, such as by joining the member directly to an element, or can be indirect, such as by means of another member disposed between the member and the element.

"Permanently bonded" refers to the joining, adhering, connecting, attaching, or the like, of two elements of an article such that the elements tend to be and remain bonded during normal use conditions of the article.

"Refastenable" refers to the property of two elements being capable of releasable attachment, separation, and subsequent releasable reattachment without substantial permanent deformation or rupture.

"Releasably attached," "releasably engaged" and variations thereof refer to two elements being connected or connectable such that the elements tend to remain connected absent a separation force applied to one or both of the elements, and the elements being capable of separation without substantial permanent deformation or rupture. The required separation force is typically beyond that encountered while wearing the article.

"Stretch bonded" refers to an elastic member being bonded to another member while the elastic member is extended at least about 25 percent of its relaxed length. More suitably, the term "stretch bonded" refers to the situation wherein the elastic member is extended at least about 100 percent, and even more suitably at least about 300 percent, of its relaxed length when it is bonded to the other member.

"Stretch bonded laminate" refers to a composite material having at least two layers in which one layer is a gatherable layer and the other layer is an elastic layer. The layers are joined together when the elastic layer is in an extended condition so that upon relaxing the layers, the gatherable layer is gathered.

These terms may be defined with additional language in the remaining portions of the specification.

BRIEF DESCRIPTION OF THE DRAWINGS

FIG. 12 is a plan view similar to FIG. 2 with an eighth embodiment of a graphic of the present invention applied to the pants;

Corresponding reference characters indicate corresponding parts throughout the drawings.

DETAILED DESCRIPTION OF THE PREFERRED EMBODIMENTS

Figure 1:
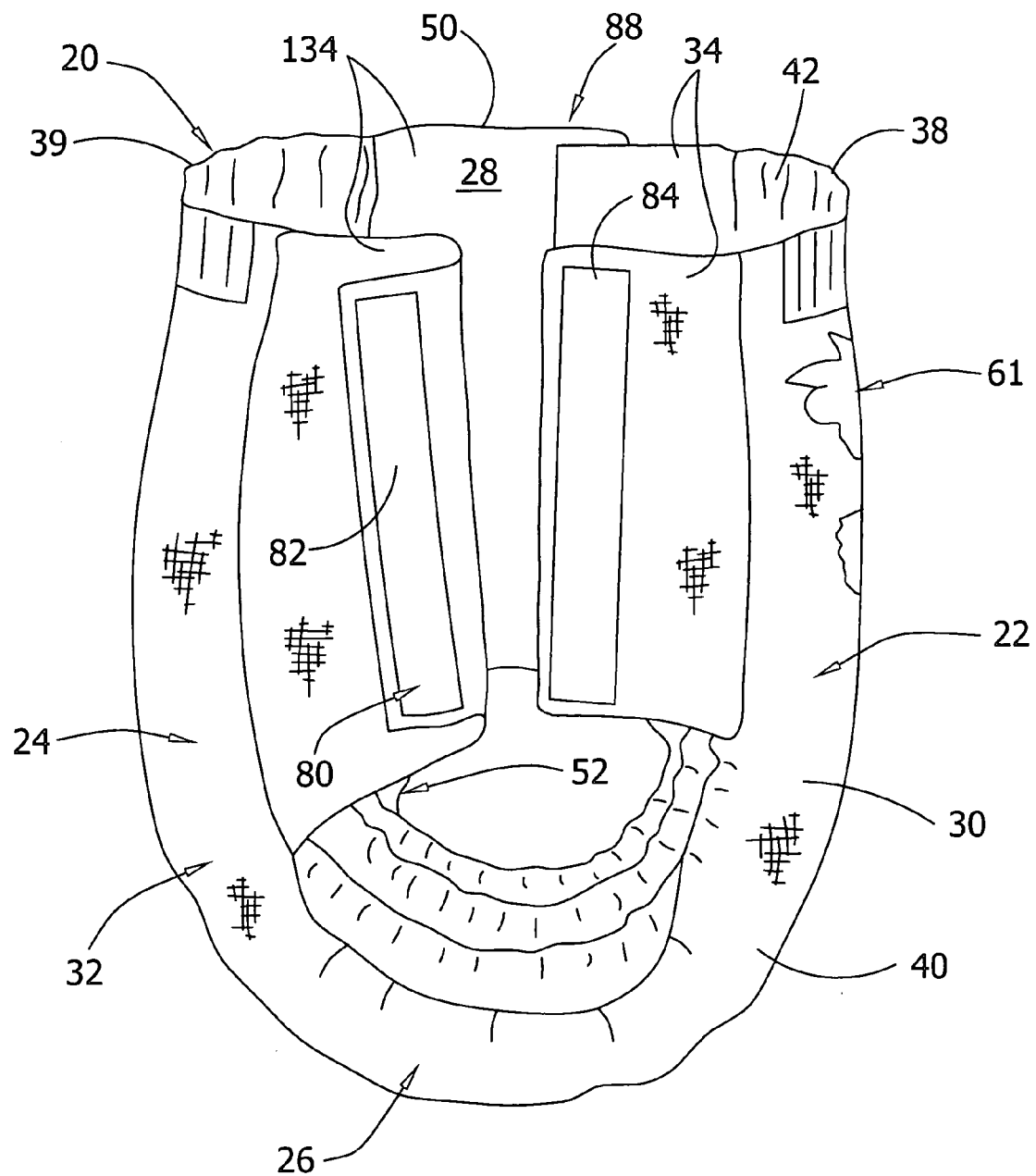
FIG. 1 is a side view of a pair of training pants with a mechanical fastening system of the pants shown fastened on one side of the training pants and unfastened on the other side of the training pants.

Referring now to the drawings and in particular to FIG. 1, a disposable article in the form of children's toilet training pants is indicated in its entirety by the reference numeral 20. The article may or may not be absorbent, which generally refers to absorbent articles that may be placed against or in proximity to the body of the wearer to absorb and/or retain various liquid waste discharged from the body. The term "disposable" as used herein refers to articles that are intended to be discarded after a limited period of use instead of being laundered or otherwise restored for reuse. It is understood that the present invention is suitable for use with various other articles such as diapers, feminine hygiene products, incontinence products, medical articles such as medical garments, surgical pads and bandages, other personal care or health care garments, apparel for institutional, industrial or consumer use, and the like without departing from the scope of the present invention.

By way of illustration only, various materials and methods for constructing the training pants 20 are disclosed in PCT Patent Application WO 00/37009 published Jun. 29, 2000 by A. Fletcher et al; U.S. Pat. No. 4,940,464 issued Jul. 10, 1990 to Van Gompel et al.; and U.S. Pat. No. 5,766,389 issued Jun. 16, 1998 to Brandon et al., which are incorporated herein by reference.

The pair of training pants 20 is illustrated in FIG. 1 in a partially fastened condition and comprises a front waist region 22, a back waist region 24, a crotch region 26 interconnecting the front and back waist regions, an inner surface 28 configured for contiguous relationship with the wearer, and an outer surface 30 opposite the inner surface. With additional reference to FIGS. 2 and 3, the training pants 20 also has a pair of laterally opposite side edges 36 and a pair of longitudinally opposite waist edges, respectively designated front waist edge 38 and back waist edge 39. The front waist region 22 is contiguous with the front waist edge 38, and the back waist region 24 is contiguous with the back waist edge 39.

Figure 2:
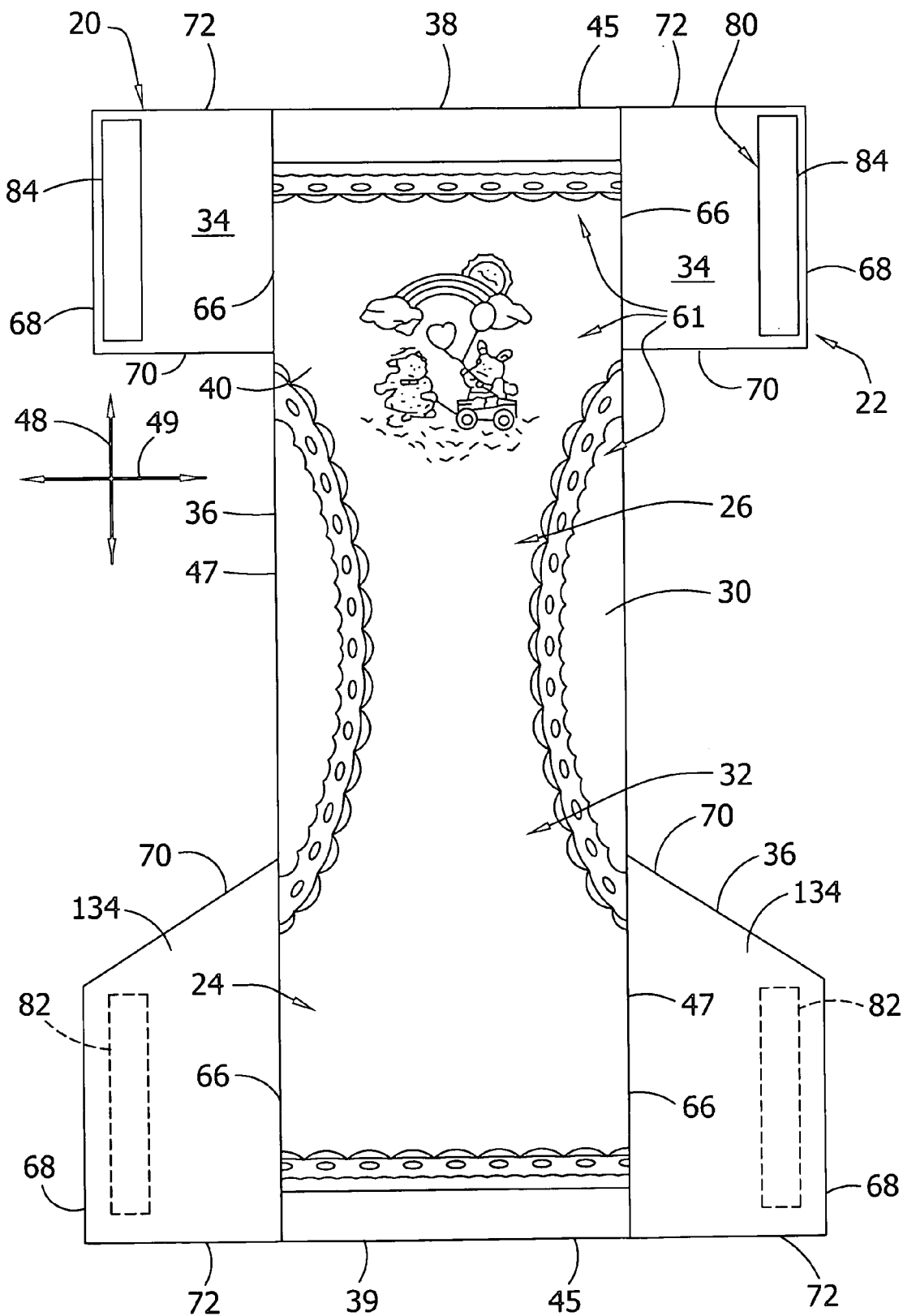
FIG. 2 is a plan view of the training pants of FIG. 1 in an unfastened, stretched and laid flat condition, and showing the surface of the training pants that faces away from the wearer.
Figure 3:
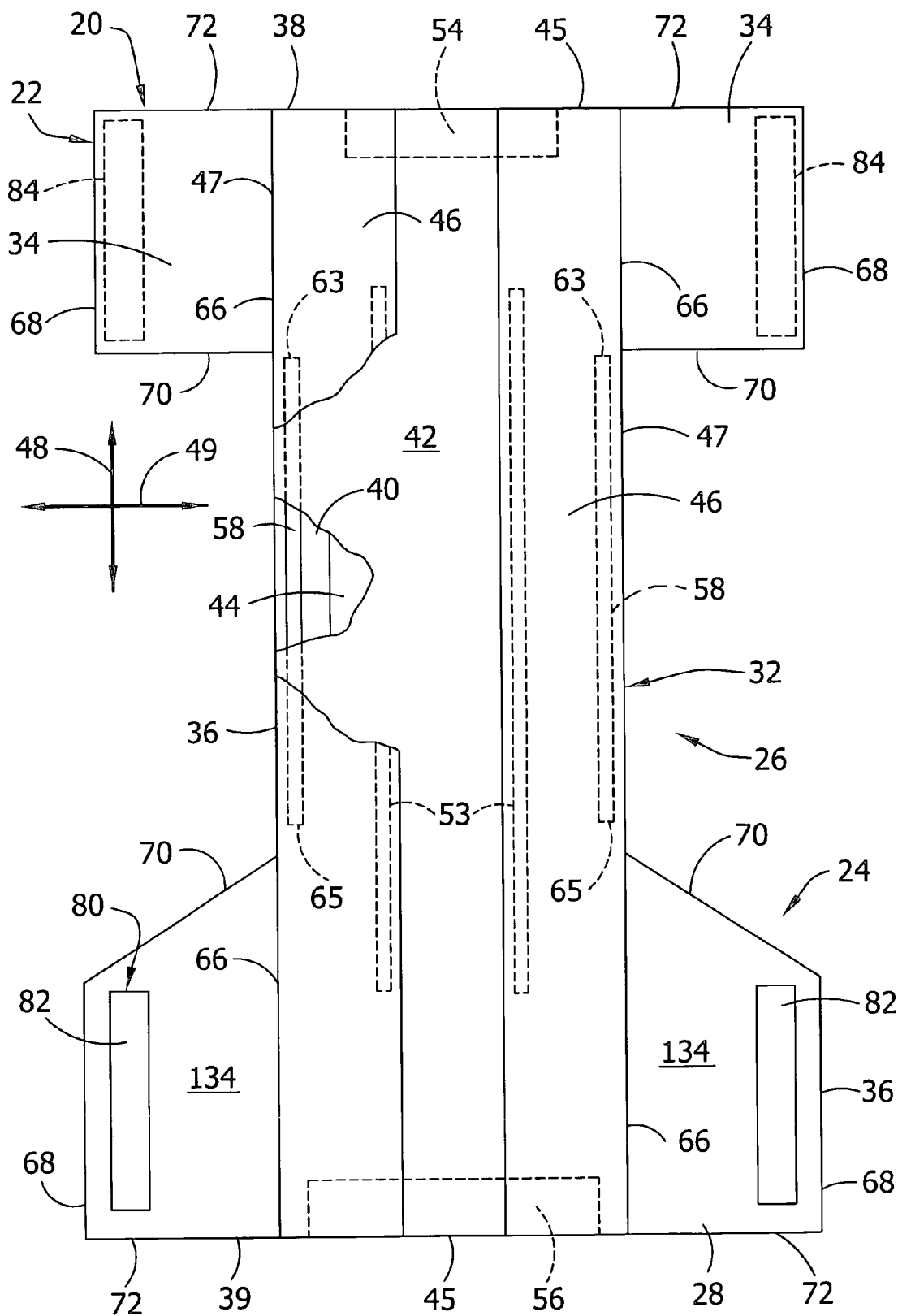
FIG. 3 is a plan view similar to FIG. 2, but showing the surface of the training pants that faces the wearer when worn, and with portions cut away to show underlying features.

The illustrated pants 20 comprises a central absorbent assembly, generally indicated at 32, which when laid flat can be rectangular or any other desired shape, a pair of laterally opposite front side panels 34 extending outward therefrom at the front waist region 22 and a pair of laterally opposite back side panels 134 extending outward therefrom at the back waist region 24. The absorbent assembly 32 and side panels 34, 134 may comprise two or more separate elements, as shown in FIG. 1, or be integrally formed. The central absorbent assembly 32 of the illustrated embodiment comprises an outer cover 40, a bodyside liner 42 (FIGS. 1 and 3) connected to the outer cover in a superposed relation, an absorbent body 44 (FIG. 3) disposed between the outer cover and the bodyside liner, and a pair of containment flaps 46 (FIG. 3). The central absorbent assembly also has opposite ends 45 which form portions of the front and back waist edges 38 and 39, and opposite side edges 47 which form portions of the side edges 36 of the training pants 20 (FIGS. 2 and 3). Integrally formed side panels 34, 134 and absorbent assembly 32 would comprise at least some common materials, such as the bodyside liner, flap composite, outer cover, other materials and/or combinations thereof, and could define a one-piece elastic, stretchable, or nonstretchable pants. For further reference, arrows 48 and 49 depict the orientation of the longitudinal axis and the transverse or lateral axis, respectively, of the training pants 20.

With the training pants 20 in the fastened position as partially illustrated in FIG. 1, the front and back side panels 34, 134 are connected together by a fastening system 80 to define a three-dimensional pants configuration having a waist opening 50 and a pair of leg openings 52. The front waist region 22 comprises the portion of the training pants 20 which, when worn, is positioned on the front of the wearer while the back waist region 24 comprises the portion of the training pants which is positioned on the back of the wearer. The crotch region 26 of the training pants 20 comprises the portion of the training pants 20 which is positioned between the legs of the wearer and covers the lower torso of the wearer. The front and back side panels 34 and 134 comprise the portions of the training pants 20 which, when worn, are positioned on the hips of the wearer. The waist edges 38 and 39 of the training pants 20 are configured to encircle the waist of the wearer and together define the waist opening 50 (FIG. 1). Portions of the side edges 36 in the crotch region 26 generally define the leg openings 52.

The central absorbent assembly 32 is configured to contain and/or absorb exudates discharged from the wearer. For example, the containment flaps 46 are configured to provide a barrier to the transverse flow of body exudates. A flap elastic member 53 (FIG. 3) can be operatively joined with each containment flap 46 in any suitable manner as is well known in the art. The elasticized containment flaps 46 define a partially unattached edge which assumes an upright configuration in at least the crotch region 26 of the training pants 20 to form a seal against the wearer's body. The containment flaps 46 can be located along the side edges 36 of the pants 20, and can extend longitudinally along the entire length of the absorbent assembly 32 or may only extend partially along the length of the absorbent assembly. Suitable constructions and arrangements for the containment flaps 46 are generally well known to those skilled in the art and are described in U.S. Pat. No. 4,704,116 issued Nov. 3, 1987 to Enloe, which is incorporated herein by reference.

To further enhance containment and/or absorption of body exudates, the training pants 20 also suitably includes a front waist elastic member 54 (FIG. 3), a rear waist elastic member 56, and leg elastic members 58, as are known to those skilled in the art. The waist elastic members 54 and 56 can be operatively joined to the outer cover 40 and/or the bodyside liner 42 along the opposite waist edges 38 and 39, and can extend over part or all of the waist edges. The leg elastic members 58 can be operatively joined to the outer cover 40 and/or the bodyside liner 42 along the opposite side edges 36 and positioned in the crotch region 26 of the training pants 20. The leg elastic members 58 can be longitudinally aligned along each side edge 47 of the absorbent assembly 32. Each leg elastic member 58 has a front terminal point 63 and a back terminal point 65, which represent the longitudinal ends of the elastic gathering caused by the leg elastic members.

The flap elastic members 53, the waist elastic members 54 and 56, and the leg elastic members 58 can be formed of any suitable elastic material. As is well known to those skilled in the art, suitable elastic materials include sheets, strands or ribbons of natural rubber, synthetic rubber, or thermoplastic elastomeric polymers. The elastic materials can be stretched and adhered to a substrate, adhered to a gathered substrate, or adhered to a substrate and then elasticized or shrunk, for example with the application of heat, such that elastic retractive forces are imparted to the substrate. In one particular embodiment, for example, the leg elastic members 58 comprise a plurality of dry-spun coalesced multifilament spandex elastomeric threads sold under the trade name LYCRA® and available from E. I. Du Pont de Nemours and Company, Wilmington, Del., U.S.A.

The outer cover 40 desirably comprises a material which is substantially liquid impermeable, and can be elastic, stretchable or nonstretchable. The outer cover 40 can be a single layer of liquid impermeable material, but desirably comprises a multi-layered laminate structure in which at least one of the layers is liquid impermeable. For instance, the outer cover 40 can include a liquid permeable outer layer and a liquid impermeable inner layer that are suitably joined together by a laminate adhesive, ultrasonic bonds, thermal bonds, or the like. Suitable laminate adhesives, which can be applied continuously or intermittently as beads, a spray, parallel swirls, or the like, can be obtained from Findley Adhesives, Inc., of Wauwatosa, Wis., U.S.A., or from National Starch and Chemical Company, Bridgewater, N.J. U.S.A. The liquid permeable outer layer can be any suitable material and is desirably one that provides a generally cloth-like texture. One example of such a material is a 20 gsm (grams per square meter) spunbond polypropylene nonwoven web. The outer layer may also be made of those materials of which the liquid permeable bodyside liner 42 is made. While it is not a necessity for the outer layer to be liquid permeable, it is desired that it provides a relatively cloth-like texture to the wearer.

The inner layer of the outer cover 40 can be both liquid and vapor impermeable, or it may be liquid impermeable and vapor permeable. The inner layer can be manufactured from a thin plastic film, although other flexible liquid impermeable materials may also be used. The inner layer, or the liquid impermeable outer cover 40 when a single layer, prevents waste material from wetting articles, such as bed sheets and clothing, as well as the wearer and caregiver. A suitable liquid impermeable film for use as a liquid impermeable inner layer, or a single layer liquid impermeable outer cover 40, is a 0.02 millimeter polyethylene film commercially available from Pliant Corporation of Schaumburg, Ill., U.S.A.

If the outer cover 40 is a single layer of material, it can be embossed and/or matte finished to provide a more cloth-like appearance. As earlier mentioned, the liquid impermeable material can permit vapors to escape from the interior of the disposable absorbent article, while still preventing liquids from passing through the outer cover 40. A suitable "breathable" material is composed of a microporous polymer film or a nonwoven fabric that has been coated or otherwise treated to impart a desired level of liquid impermeability. A suitable microporous film is a PMP-1 film material commercially available from Mitsui Toatsu Chemicals, Inc., Tokyo, Japan, or an XKO-8044 polyolefin film commercially available from 3M Company, Minneapolis, Minn. U.S.A.

The liquid permeable bodyside liner 42 is illustrated as overlying the outer cover 40 and absorbent body 44, and may but need not have the same dimensions as the outer cover 40. The bodyside liner 42 is desirably compliant, soft feeling, and non-irritating to the child's skin. Further, the bodyside liner 42 can be less hydrophilic than the absorbent body 44, to present a relatively dry surface to the wearer and permit liquid to readily penetrate through its thickness. Alternatively, the bodyside liner 42 can be more hydrophilic or can have essentially the same affinity for moisture as the absorbent body 44 to present a relatively wet surface to the wearer to increase the sensation of being wet. This wet sensation can be useful as a training aid. The hydrophilic/hydrophobic properties can be varied across the length, width and depth of the bodyside liner 42 and absorbent body 44 to achieve the desired wetness sensation or leakage performance.

The bodyside liner 42 can be manufactured from a wide selection of web materials, such as synthetic fibers (for example, polyester or polypropylene fibers), natural fibers (for example, wood or cotton fibers), a combination of natural and synthetic fibers, porous foams, reticulated foams, apertured plastic films, or the like. Various woven and nonwoven fabrics can be used for the bodyside liner 42. For example, the bodyside liner can be composed of a meltblown or spunbonded web of polyolefin fibers. The bodyside liner can also be a bonded-carded web composed of natural and/or synthetic fibers. The bodyside liner can be composed of a substantially hydrophobic material, and the hydrophobic material can, optionally, be treated with a surfactant or otherwise processed to impart a desired level of wettability and hydrophilicity. For example, the material can be surface treated with about 0.45 weight percent of a surfactant mixture comprising Ahcovel N-62 from Hodgson Textile Chemicals of Mount Holly, N.C., U.S.A. and Glucopan 220UP from Henkel Corporation of Ambler, Pa. in an active ratio of 3:1. The surfactant can be applied by any conventional means, such as spraying, printing, brush coating or the like. The surfactant can be applied to the entire bodyside liner 42 or can be selectively applied to particular sections of the bodyside liner, such as the medial section along the longitudinal center line.

A suitable liquid permeable bodyside liner 42 is a nonwoven bicomponent web having a basis weight of about 27 gsm. The nonwoven bicomponent can be a spunbond bicomponent web, or a bonded carded bicomponent web. Suitable bicomponent fibers include a polyethylene/polypropylene bicomponent fiber available from CHISSO Corporation, Osaka, Japan. In this particular bicomponent fiber, the polypropylene forms the core and the polyethylene forms the sheath of the fiber. Other fiber orientations are possible, such as multi-lobe, side-by-side, end-to-end, or the like.

The absorbent body 44 (FIG. 3) is positioned between the outer cover 40 and the bodyside liner 42, which can be joined together by any suitable means such as adhesives, ultrasonic bonds, thermal bonds, or the like. The absorbent body 44 can be any structure which is generally compressible, conformable, non-irritating to the child's skin, and capable of absorbing and retaining liquids and certain body wastes, and may be manufactured in a wide variety of sizes and shapes, and from a wide variety of liquid absorbent materials commonly used in the art. For example, the absorbent body 44 can suitably comprise a matrix of hydrophilic fibers, such as a web of cellulosic fluff, mixed with particles of a high-absorbency material commonly known as superabsorbent material. In a particular embodiment, the absorbent body 44 comprises a matrix of cellulosic fluff, such as wood pulp fluff, and superabsorbent hydrogel-forming particles. The wood pulp fluff can be exchanged with synthetic, polymeric, meltblown fibers or short cut homofil bicomponent synthetic fibers and natural fibers. The superabsorbent particles can be substantially homogeneously mixed with the hydrophilic fibers or can be non-uniformly mixed. The fluff and superabsorbent particles can also be selectively placed into desired zones of the absorbent body 44 to better contain and absorb body exudates. The concentration of the superabsorbent particles can also vary through the thickness of the absorbent body 44. Alternatively, the absorbent body 44 can comprise a laminate of fibrous webs and superabsorbent material or other suitable means of maintaining a superabsorbent material in a localized area.

Suitable superabsorbent materials can be selected from natural, synthetic, and modified natural polymers and materials. The superabsorbent materials can be inorganic materials, such as silica gels, or organic compounds, such as crosslinked polymers, for example, sodium neutralized polyacrylic acid. Suitable superabsorbent materials are available from various commercial vendors, such as Dow Chemical Company located in Midland, Mich., U.S.A., and Stockhausen GmbH & Co. KG, D-47805 Krefeld, Federal Republic of Germany. Typically, a superabsorbent material is capable of absorbing at least about 10 times its weight in water, and suitably is capable of absorbing more than about 25 times its weight in water.

In one embodiment, the absorbent body 44 comprises a blend of wood pulp fluff and superabsorbent material. One preferred type of pulp is identified with the trade designation CR1654, available from U.S. Alliance, Childersburg, Ala., U.S.A., and is a bleached, highly absorbent sulfate wood pulp containing primarily soft wood fibers and about 16 percent hardwood fibers. As a general rule, the superabsorbent material is present in the absorbent body 44 in an amount of from 0 to about 90 weight percent based on total weight of the absorbent assembly. The absorbent body 44 suitably has a density within the range of about 0.10 to about 0.35 grams per cubic centimeter. The absorbent body 44 may or may not be wrapped or encompassed by a suitable tissue wrap that may help maintain the integrity and/or shape of the absorbent assembly.

The central absorbent assembly 32 can also incorporate other materials or components designed primarily to receive, temporarily store, and/or transport liquid along the mutually facing surface with the absorbent body 44, thereby maximizing the absorbent capacity of the absorbent assembly. One suitable additional component is commonly referred to as a surge layer (not shown) and comprises a material having a basis weight of about 50 to about 120 grams per square meter, and more particularly comprises a through-air-bonded-carded web of a homogenous blend of 60 percent 3 denier type T-256 bicomponent fiber comprising a polyester core/polyethylene sheath and 40 percent 6 denier type T-295 polyester fiber, both commercially available from Kosa Corporation of Salisbury, N.C., U.S.A.

As noted previously, the illustrated training pants 20 have front and back side panels 34 and 134 disposed on each side of the absorbent assembly 32. The side panels 34, 134 can be permanently bonded along seams 66 to the central absorbent assembly 32 in the respective front and back waist regions 22 and 24. More particularly, as seen best in FIGS. 2 and 3, the front side panels 34 can be permanently bonded to and extend transversely outward beyond the side edges 47 of the absorbent assembly 32 in the front waist region 22, and the back side panels 134 can be permanently bonded to and extend transversely outward beyond the side edges of the absorbent assembly in the back waist region 24. The side panels 34 and 134 may be bonded to the absorbent assembly 32 using attachment means known to those skilled in the art such as adhesive, thermal or ultrasonic bonding. Alternatively, the side panels 34 and 134 can be formed as an integral portion of a component of the absorbent assembly 32. For example, the side panels can comprise a generally wider portion of the outer cover 40, the bodyside liner 42, and/or another component of the absorbent assembly 32. The front and back side panels 34 and 134 can be permanently bonded together or be releasably connected with one another such as by the fastening system 80 of the illustrated embodiment.

The front and back side panels 34, 134 each have an outer edge 68 spaced laterally from the seam 66, a leg end edge 70 disposed toward the longitudinal center of the training pants 20, and a waist end edge 72 disposed toward a longitudinal end of the training pants. The leg end edge 70 and waist end edge 72 extend from the side edges 47 of the absorbent assembly 32 to the outer edges 68. The leg end edges 70 of the side panels 34 and 134 form part of the side edges 36 of the training pants 20. The leg end edges 70 of the illustrated embodiment are suitably curved and/or angled relative to the transverse axis 49 to provide a better fit around the wearer's legs. However, it is understood that only one of the leg end edges 70 may be curved or angled, such as the leg end edge of the back waist region 24, or neither of the leg end edges may be curved or angled, without departing from the scope of this invention. The waist end edges 72 are suitably parallel to the transverse axis 49. The waist end edges 72 of the front side panels 34 form part of the front waist edge 38 of the training pants 20, and the waist end edges 72 of the back side panels 134 form part of the back waist edge 39 of the pants.

The side panels 34, 134 suitably, although not necessarily, comprise an elastic material capable of stretching in a direction generally parallel to the transverse axis 49 of the training pants 20. Suitable elastic materials, as well as one process of incorporating elastic side panels into training pants, are described in the following U.S. Pat. No. 4,940,464 issued Jul. 10, 1990 to Van Gompel et al.; U.S. Pat. No. 5,224,405 issued Jul. 6, 1993 to Pohjola; U.S. Pat. No. 5,104,116 issued Apr. 14, 1992 to Pohjola; and U.S. Pat. No. 5,046,272 issued Sep. 10, 1991 to Vogt et al.; all of which are incorporated herein by reference. In particular embodiments, the elastic material may comprise a stretch-thermal laminate (STL), a neck-bonded laminate (NBL), a reversibly necked laminate, or a stretch-bonded laminate (SBL) material. Methods of making such materials are well known to those skilled in the art and described in U.S. Pat. No. 4,663,220 issued May 5, 1987 to Wisneski et al.; U.S. Pat. No. 5,226,992 issued Jul. 13, 1993 to Morman; European Patent Application No. EP 0 217 032 published on Apr. 8, 1987 in the name of Taylor et al.; and PCT application WO 01/88245 in the name of Welch et al.; all of which are incorporated herein by reference. Alternatively, the side panel material may comprise other woven or nonwoven materials, such as those described above as being suitable for the outer cover 40 or bodyside liner 42; mechanically pre-strained composites; or stretchable but inelastic materials.

The fastening system 80 comprises laterally opposite first fastening components 82 adapted for refastenable engagement to corresponding second fastening components 84. In one embodiment, a front or outer surface of each of the fastening components 82, 84 comprises a plurality of engaging elements. The engaging elements of the first fastening components 82 are adapted to repeatedly engage and disengage corresponding engaging elements of the second fastening components 84 to releasably secure the pants 20 in its three-dimensional configuration.

The fastening components 82, 84 can comprise any refastenable fasteners suitable for absorbent articles, such as adhesive fasteners, cohesive fasteners, mechanical fasteners, or the like. In particular embodiments the fastening components comprise mechanical fastening elements for improved performance. Suitable mechanical fastening elements can be provided by interlocking geometric shaped materials, such as hooks, loops, bulbs, mushrooms, arrowheads, balls on stems, male and female mating components, buckles, snaps, or the like.

In the illustrated embodiment, the first fastening components 82 comprise loop fasteners and the second fastening components 84 comprise complementary hook fasteners. Alternatively, the first fastening components 82 may comprise hook fasteners and the second fastening components 84 may comprise complementary loop fasteners. In another embodiment, the fastening components 82, 84 can comprise interlocking similar surface fasteners, or adhesive and cohesive fastening elements such as an adhesive fastener and an adhesive-receptive landing zone or material; or the like. Although the training pants 20 illustrated in FIG. 1 show the back side panels 134 overlapping the front side panels 34 upon connection thereto, which is convenient, the training pants 20 can also be configured so that the front side panels overlap the back side panels when connected. One skilled in the art will recognize that the shape, density and polymer composition of the hooks and loops may be selected to obtain the desired level of engagement between the fastening components 82, 84. A more aggressive hook material may comprise a material with a greater average hook height and/or a greater percentage of directionally-aligned hooks.

Loop fasteners typically comprise a fabric or material including a plurality of loop members. The loop material can be formed of any suitable material, such as acrylic, polyamide, polyethylene, polypropylene or polyester, and can be formed by methods such as warp knitting, stitch bonding or needle punching. Loop materials can also comprise any fibrous structure capable of entangling or catching hook materials, such as carded, spunbonded or other nonwoven webs or composites, including elastomeric and nonelastomeric composites. Suitable loop materials are available from Guilford Mills, Inc., Greensboro, N.C., U.S.A. under the trade designation No. 36549. Another suitable loop material can comprise a pattern un-bonded web as disclosed in co-assigned U.S. Pat. No. 5,858,515 issued Jan. 12, 1999 to Stokes et al. incorporated herein by reference. The loop material may be secured to a base, or backing structure and the composite then secured to the pants 20, or the loop material may be secured directly to the pants so that the pair of pants serves as a backing for the loop material, or the loop material may be formed integrally with the pants, such as by constructing one or more layers or surfaces of the back side panels 134 from a loop material.

Hook fasteners typically comprise a fabric or material having a base or backing structure and a plurality of hook members extending upwardly from at least one surface of the backing structure. It should be understood that the term "hook" as used in reference to the hook members is non-limiting in the sense that the engaging elements of the hook fasteners may comprise shapes such as hooks, "T's", "mushrooms" or any other shape so long as they are adapted to releasably engage the loop fasteners so as to provide a secure, but non-destructively releasable engagement. In contrast to the loop fasteners which suitably comprise a flexible fabric, the hook material may advantageously comprise a resilient material to minimize unintentional disengagement of the fastening components 82, 84 as a result of the hook material becoming deformed and catching on clothing or other items. The term "resilient" as used herein refers to an interlocking material having a predetermined shape and the property of the interlocking material to resume the predetermined shape after being engaged and disengaged from a mating, complementary interlocking material.

Suitable hook material can be molded or extruded from nylon, polypropylene, polyethylene or another suitable material. Suitable single-sided hook materials for the fastening components are available from commercial vendors such as Velcro Industries B.V., Amsterdam, Netherlands or affiliates thereof, identified as Velcro HTH-829, which has a thickness of about 0.9 millimeters (35 mils) and HTH-851, which has a thickness of about 0.5 millimeters (20 mils); and Minnesota Mining & Manufacturing Co., St. Paul, Minn. U.S.A., including specific materials identified as CS-600. As with the loop fastener, it is understood that the hook material may formed integrally with the pants 20, and more particularly with the side panels 34, without departing from the scope of this invention.

With particular reference to FIG. 3, the first fastening components 82 (e.g., the loop fasteners) are disposed on the inner surface 28 of the back side panels 134, and are suitably positioned adjacent the outer edges 68 of the back side panels 134. The second fastening components 84 (e.g., the hook fasteners) are disposed on the outer surface 30 of the front side panels 34 adjacent the outer edges 68 thereof as shown in FIG. 2, and are suitably sized to receive the first fastening components 82.

It is understood that the fastening components 82, 84 may also extend laterally out beyond the outer edges 68 of the side panels 134, 34. Where the first fastening components 82 comprise loop fasteners disposed on the inner surface 28 and the second fastening components 84 comprise hook fasteners disposed on the outer surface 30, the first fastening components can be sized larger than the second fastening components to ensure coverage of the rigid, outwardly-directed hooks.

The fastening components 82, 84 of the illustrated embodiments are rectangular, although they may alternatively be square, round, oval, curved or other suitable shapes. In particular embodiments, each of the fastening components 82, 84 has a length aligned generally parallel to the longitudinal axis 48 of the training pants 20 and a width aligned generally parallel to the transverse axis 49 of the training pants. For a child of about 9 to about 15 kilograms (20–30 pounds), for example, the length of the fastening components 82, 84 is desirably from about 50 to about 130 mm, such as about 100 mm, and the width is desirably from about 5 to about 30 mm, such as about 10 mm. In particular embodiments, the fastening components 82, 84 can have a length-to-width ratio of about 2 or greater, such as about 2 to about 25, and more particularly about 5 or greater, such as about 5 to about 8. For other embodiments such as for adult products, it may be desirable for one or more of the fastening components to comprise a plurality of relatively smaller fastening elements. In that case, a fastening component or individual fastening elements may have an even smaller length-to-width ratio, for example, of about 2 or less, and even about 1 or less.

The fastening components 84, 82 are suitably secured to the respective side panels 34, 134 by mechanical bonding. As used herein, mechanical bonding refers to non-adhesive bonding, such as by the application of pressure, ultrasonic energy, heat, laser energy or any other suitable form of energy which joins the fastening components to the side panels. It is understood that the fastening components 84, 82 may be adhered, such as by adhesive or cohesive means, to the respective side panels 34, 134 in addition to being mechanically bonded thereto, or the fastening components may only be mechanically bonded to the side panels, without departing from the scope of this invention. Where a fastening component 82, 84 is formed integrally with the respective side panel 134, 34, mechanical bonding may be omitted or may comprise mechanically bonding the fastener material layer of the side panel to one more other layers or surfaces of the side panel.

As shown in FIG. 1, when the fastening components 82, 84 are releasably engaged, the side edges 36 of the training pants 20 in the crotch region 26 define the leg openings 52, and the waist edges 38 and 39 including the waist end edges 72 of the side panels 34, 134 define the waist opening 50. For improved formation of the leg openings 52, it can be desirable in some embodiments for the front side panels 34 to be longitudinally spaced from the back side panels 134 as shown in FIGS. 2 and 3. For example, the front side panels 34 can be longitudinally spaced from the back side panels 134 by a distance equal to about 20 percent or greater, particularly from about 20 to about 60 percent, and more particularly from about 35 to about 50 percent, of the overall length of the pants 20.

When engaged, the fastening components 82, 84 of the illustrated embodiment define refastenable engagement seams 88 (FIG. 1) which desirably although not necessarily extend substantially the entire distance between the waist opening 50 and the leg openings 52. More specifically, the engagement seams 88 can cover about 70 to 100 percent, and particularly about 85 to about 95 percent, of the distance between the waist opening 50 and each leg opening 52, which distance is measured parallel to the longitudinal axis 48. To construct the engagement seams 88 to extend substantially the entire distance between the waist and leg openings 50 and 52, the fastening components 82, 84 can be formed to cover about 70 to 100 percent, and more particularly about 85 to about 95 percent, of the distance between the waist end edge 70 and the leg end edge 72 of the side panels 34, 134. In other embodiments, the fastening components can comprise a plurality of smaller fastening elements (not shown) covering a smaller portion of the distance between the waist opening 50 and the leg openings 52, for example, about 20 to about 70 percent, but spaced apart to span a larger percentage of the distance between the waist opening and the leg openings.

For the engagement seams 88 to be located at the sides of the wearer, it can be particularly desirable for the transverse distance between the fastening components 82 of the back side panels 134 to be substantially equal to the transverse distance between the fastening components 84 of the front side panel 134. The transverse distance between each respective set of fastening components 82, 84 is measured parallel to the transverse axis 49 between the longitudinal center lines of the respective fastening components, measured with the side panels 34, 134 in an unstretched condition. Alternatively, the lateral spacing between the fastening components 82 may be greater or less than the lateral spacing between the fastening components 84. It is also contemplated that fastening components 82 (and/or the fastening components 84) may not be laterally opposite each other, or may be only partially laterally opposite each other, such as by being offset longitudinally.

As shown in FIGS. 1 and 2, the training pants 20, and in particular the outer cover 40 thereof, includes one or more graphics, generally indicated at 61, at least one of which suitably comprises a graphic of the present invention. Examples of such graphics include, but are not limited to, scenes, characters, animals, objects, alphanumerics such as numbers, letters, words, phrases and the like, highlighting or emphasizing leg and waist openings 52, 50 in order to make product shaping more evident or visible to the user; highlighting or emphasizing areas of the product to simulate functional components such as elastic leg bands, elastic waistbands, simulated "fly openings" for boys, ruffles for girls; highlighting areas of the product to change the appearance of the size of the product; registering wetness indicators, temperature indicators, and the like in the product; registering a back label, or a front label, in the product; and registering written instructions at a desired location in the product. The graphics 61 are suitably positioned on the training pants 20 at selected locations, which can be carried out using the methods disclosed in U.S. Pat. No. 5,766,389 issued Jun. 16, 1998 to Brandon et al., the entire disclosure of which is incorporated herein by reference.

Figure 4:
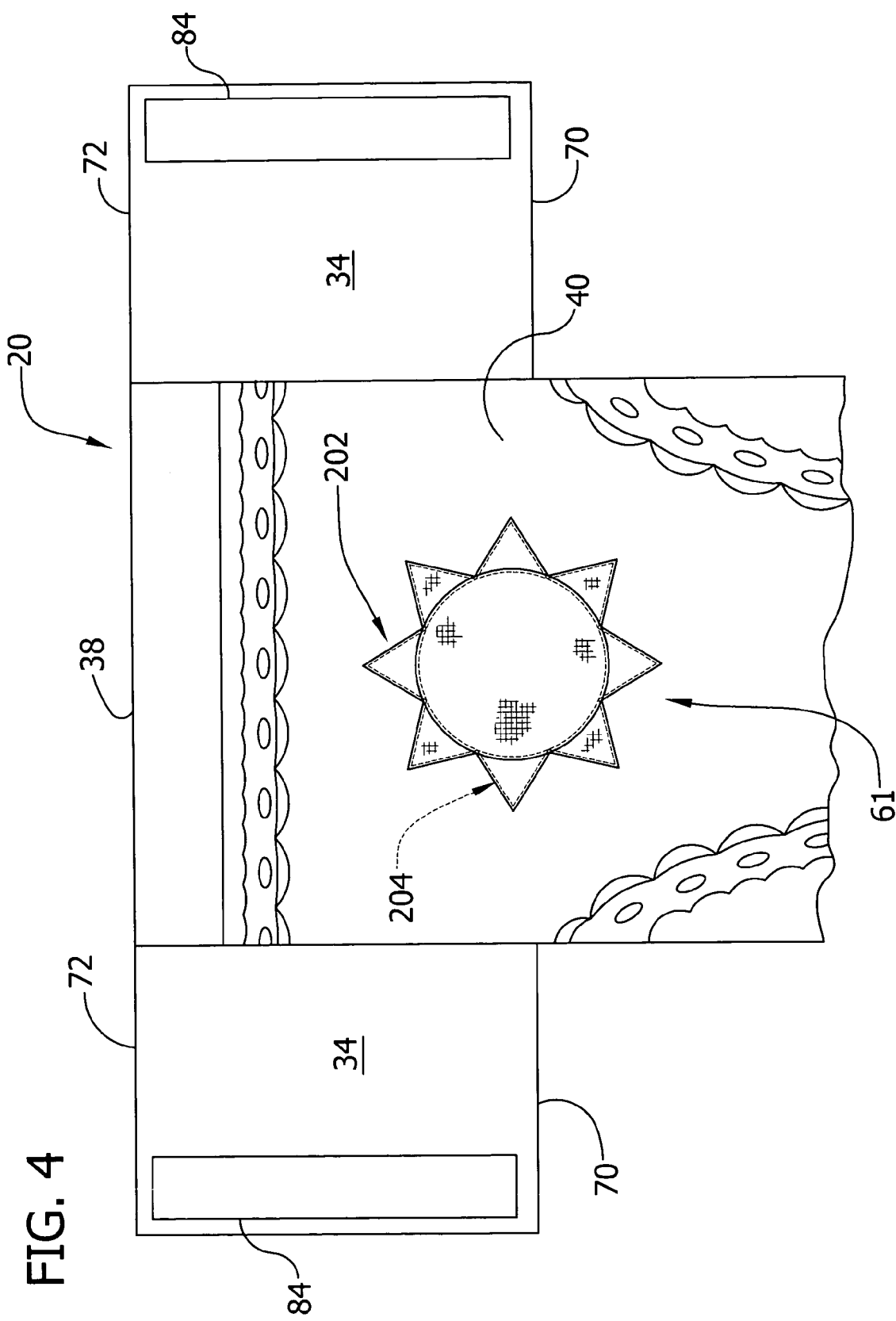
FIG. 4 is a plan view similar to FIG. 2 with one embodiment of a graphic of the present invention applied to the pants.

With particular reference to FIG. 4, in one embodiment the graphic 61 of the present invention generally comprises a non-phosphorescent region (shown in solid line in FIG. 4 and indicated generally at 202) and a phosphorescent region (shown in phantom in FIG. 4 and indicated generally at 204). As used herein, the term "phosphorescent" refers to the ability to phosphoresce, i.e., to absorb electromagnetic energy (e.g., light) from a source thereof and subsequently emit electromagnetic energy at a different wavelength than the source following removal of the electromagnetic energy source (e.g., in the absence of light). The term "non-phosphorescent" therefore refers to an inability to phosphoresce such that it becomes substantially less visible in the absence of light.

Thus, the non-phosphorescent region 202 of the graphic 61 is generally visible under "normal" light conditions (e.g., daytime or other than dimly lit conditions) but becomes substantially less visible, or is otherwise non-visible, in the absence of light. In contrast, following exposure of the phosphorescent region to light sufficient to cause phosphorescence of the phosphorescent region 204, the phosphorescent region luminesces, i.e., emits electromagnetic energy, upon the subsequent removal of light so that the phosphorescent region is visible in the absence of light, i.e., it glows in the dark. The term "visible" as used herein means visible to the human eye unaided by detecting, enhancing and/or magnifying devices.

In the illustrated embodiment of FIG. 4, the non-phosphorescent region 202 of the graphic 61 and the phosphorescent region 204 are in overlapping relationship with each other, and more particularly they are in registry with each other, to define an overlapping region of the graphic. Thus, it is to be understood that the phantom lines shown offset from the solid lines in FIG. 4 are for illustrative purposes only and suitably lie on the solid lines in registry therewith. Following exposure of the overlapping region to light sufficient to cause phosphorescence of the phosphorescent region 204, the phosphorescent region luminesces upon the subsequent removal of light so that the overlapping region is visible in the absence of light. As an example, the graphic 61 shown in FIG. 4 is a sun comprised of a yellow non-phosphorescent region 202 in registry with a phosphorescent region 204 so that the sun appears yellow during normal light conditions and subsequently glows in the absence of light.

Figure 5:
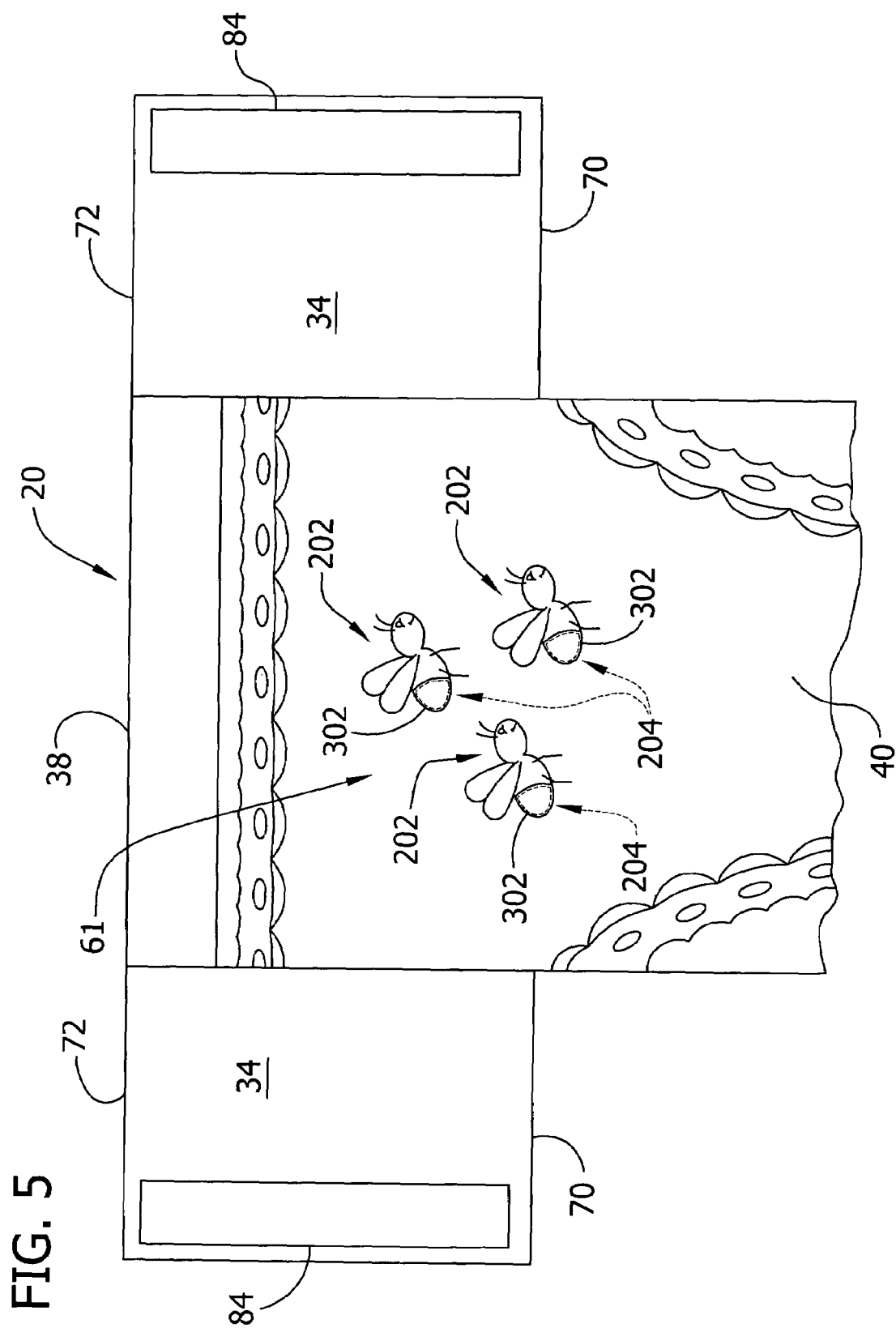
FIG. 5 is a plan view similar to FIG. 2 with a second embodiment of a graphic of the present invention applied to the pants.

It is also contemplated that the non-phosphorescent region 202 and the phosphorescent region 204 may be other than in registry with each other as long as at least a portion of the non-phosphorescent region is in overlapping relationship with at least a portion of the phosphorescent region to define an overlapping region of the graphic. The overlapping region is thus visible in normal light conditions and luminesces (e.g., glows) upon the subsequent removal of light (e.g., in the dark). As another example, the graphic 61 in the illustrated embodiment of FIG. 5 is a firefly having a rear abdomen 302. The entire firefly comprises a non-phosphorescent region 202 broadly defined by one or more colors including a yellow color of the rear abdomen 302. A phosphorescent region 204 is in overlapping relationship with the non-phosphorescent region 202 at the rear abdomen 302 so that the firefly, including the rear abdomen, is visible as a colored graphic in normal light conditions and after exposure to light sufficient to cause the phosphorescent region to phosphoresce, the rear abdomen of the firefly glows in a subsequent absence of light.

In another embodiment (FIG. 6), the non-phosphorescent region 202 defines a detail of the graphic 61 and the phosphorescent region 204 is a mirror image of the detail arranged in overlapping relationship with the non-phosphorescent region. The mirror image detail defined by the phosphorescent region 204 is suitably rotated, such as in the range of about 1 to about 359 degrees, relative to the detail defined by the phosphorescent region 202. For example, in the illustrated embodiment the mirror image detail defined by the phosphorescent region 204 is rotated approximately 180 degrees relative to the detail defined by the non-phosphorescent region 202. In such an embodiment, the non-phosphorescent region 202 is visible in normal light conditions. Upon exposure to light sufficient to cause the phosphorescent region to phosphoresce and the subsequent removal of light, the phosphorescent region 204 luminesces while the non-phosphorescent becomes substantially less visible so that the graphic 61 appears rotated (e.g., inverted in the illustrated embodiment) relative to the orientation of the graphic as it appeared in normal light conditions.

Figure 7:
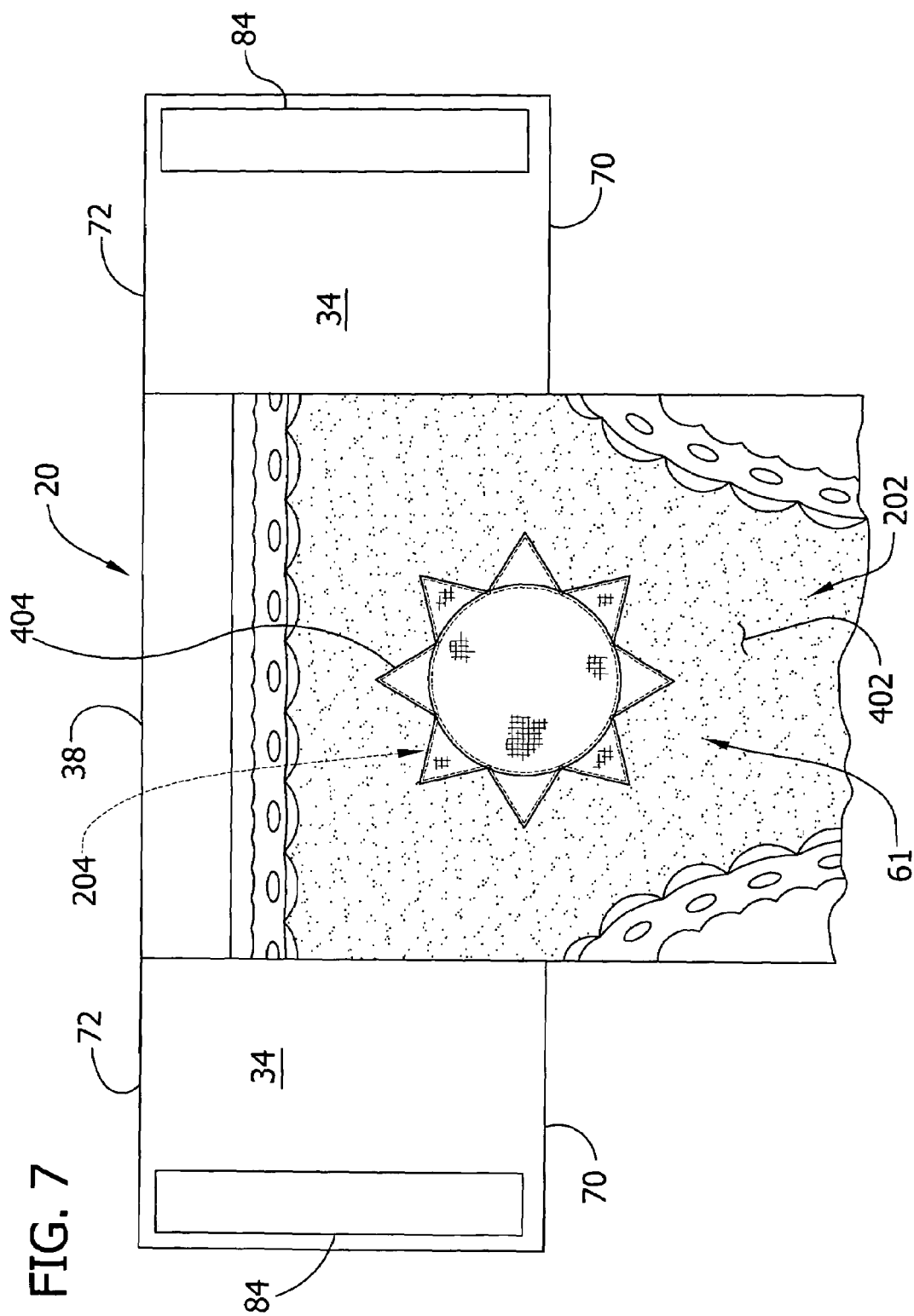
FIG. 7 is a plan view similar to FIG. 2 with a fourth embodiment of a graphic of the present invention applied to the pants.

FIG. 7 illustrates another embodiment in which the graphic 61 comprises a non-phosphorescent region 202 (which may comprise one or more colors) defining both a background 402 of the graphic as well as one or more details 404 of the graphic. One or more phosphorescent regions 204 of the graphic are disposed entirely within the non-phosphorescent region 202 in overlapping relationship, and more particularly in registry, with the details 404 of the graphic. In normal light conditions, the entire colored background 402 and details 404 of the graphic are visible, while in the subsequent absence of light only the details (e.g., the regions in which the non-phosphorescent and phosphorescent regions overlap) luminesce, or glow.

It is also contemplated that the non-phosphorescent region 202 may define only a background (e.g., background 402 of FIG. 7) of the graphic 61 and that the phosphorescent region or regions 204 may define details (e.g., detail 404 of FIG. 7) disposed entirely within the non-phosphorescent region in overlapping relationship therewith. In such an embodiment, the overlapping region or regions would be visible in normal light conditions only as the background 402 of the graphic 61, or the faint appearance of the phosphorescent region may be visible, while in a subsequent absence of light only the details 404 (the overlapping regions) would glow.

In yet another embodiment, the phosphorescent region 202 may be in overlapping relationship with the non-phosphorescent region 204 throughout all or part of the background (e.g, background 402 of FIG. 7) of the graphic 61 but be discrete from (e.g., in non-overlapping relationship with) the details (e.g., detail 404 of FIG. 7) of the graphic. In such an embodiment, the entire background 402 and details 404 of the graphic 61 are visible in normal light conditions. Upon the removal of light, the background 402 of the graphic 61 glows while the details 404 remain substantially un-illuminated so as to be recognizable against the glowing background.

It is further contemplated that the background 402 of the graphic 61 described in any of the above embodiments may comprise a vignette, i.e., the background gradually changes shades of color and/or gradually changes in glow intensity from one portion of the background to another.

In one embodiment, the non-phosphorescent region of the graphic 61 is formed by applying a non-phosphorescent material to the outer cover 40 of the pants 20, and more particularly to the inner layer (broadly, a substrate) thereof. Similarly, the phosphorescent region of the graphic 61 is formed by applying a phosphorescent material to the inner layer of the outer cover. As used herein in reference to applying the non-phosphorescent and phosphorescent materials to a substrate such as the inner layer of the outer cover 40, the terms "apply," "applying," and "applied" are intended to refer to the respective material being applied to the substrate following initial formation of the substrate, such as by imprinting, adhering, spraying, etc. onto the substrate.

More suitably, both the non-phosphorescent material and the phosphorescent material are applied to the outer face of the inner layer of the outer cover 40. However, it is understood that the non-phosphorescent material may be applied to an inner face of the inner layer of the outer cover while the phosphorescent material is applied to the outer face of the inner layer, or vice versa, as long as portions of the respective regions 202, 204 defined by the applied phosphorescent and non-phosphorescent materials are in overlapping relationship with each other to define an overlapping region. It is also contemplated that both the non-phosphorescent material and the phosphorescent material may be applied to the inner face of the inner layer of the outer cover 40 and remain within the scope of this invention.

Alternatively, both the phosphorescent material and the non-phosphorescent material may be applied to the nonwoven outer layer (also broadly referred to as a substrate) of the outer cover 40, or one of the phosphorescent material and the non-phosphorescent material may be applied to the outer layer of the outer cover while the other is applied to the inner layer of the outer cover, as long as the inner and outer layers are overlaid with each other so that the respective regions 202, 204 defined by the applied phosphorescent and non-phosphorescent materials are in overlapping relationship with each other. It is also understood that the graphic 61 may be applied to any of the other components of the training pants 20, such as the liner 42, side panels 34, 134, etc., without departing from the scope of this invention.

Figure 8:
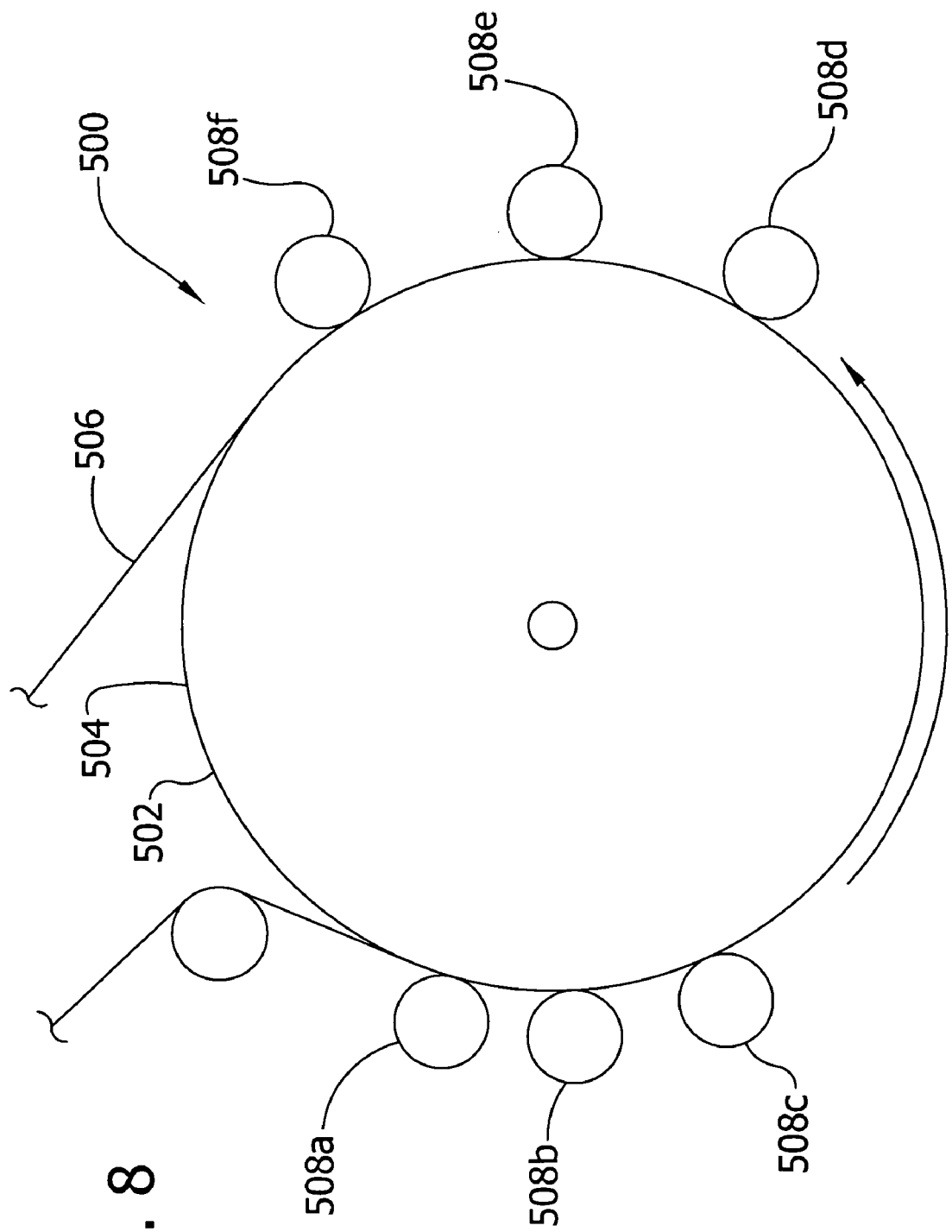
FIG. 8 is a schematic of a flexographic printing apparatus.

In one embodiment, the graphic 61 is suitably applied to the pants 20 by being imprinted thereon using a flexographic printing process. Flexographic printing is a conventional printing technique which uses flexible, raised rubber or photopolymer plates to carry an inked image to a substrate, such as the inner layer of the outer cover 40 of the pants 20. FIG. 8 schematically illustrates a suitable flexographic printing apparatus, generally indicated at 500 comprising a rotary impression cylinder 502 having a circumferential outer surface 504 on which a continuous substrate 506 (e.g., the film used as the inner layer of the outer cover 40 of the pants 20) is transported by the impression cylinder in the direction of rotation thereof as indicated by the directional arrow in FIG. 8. Rotary print cylinders (six are shown in FIG. 8 and indicated respectively at 508a, 508b, 508c, 508d, 508e and 508f) are positioned about the impression cylinder 502 in opposed relationship with the circumferential outer surface 504 of the impression cylinder. The print cylinders 508a, 508b, 508c, 508d, 508e, 508f are each moveable relative to the impression cylinder 502 between a printing position in which the print cylinder is in generally close contact relationship with the substrate 506 on the outer surface 504 of the impression cylinder to transfer an ink image onto the substrate, and a non-printing position in which the print cylinder is spaced from the substrate and the impression cylinder outer surface. Each of the print cylinders 508a, 508b, 508c, 508d, 508e, 508f carries a respective raised rubber or photopolymer plate (not shown) for transferring an ink image onto the substrate 506 in the form of a plurality of ink dots arranged in the desired pattern.

Particular construction and operation of the flexographic printing apparatus 500 is well known to those skilled in the art and will not be further described herein except to the extent necessary to describe the present invention. As an example, flexographic printing apparatus are shown and/or described in U.S. Pat. No. 5,458,590 (Schleinz et al.); U.S. Pat. No. 5,566,616 (Schleinz et al.); U.S. 2003/0019374A1 (Harte); and U.S. Pat. No. 4,896,600 (Rogge et al.).

Each of the print cylinders 508a, 508b, 508c, 508d, 508e, 508f of the flexographic printing apparatus 500 applies a different ink to the substrate 506, such as a different color ink and/or a different type of ink. As the substrate 506 passes each print cylinder 508a, 508b, 508c, 508e, 508f in the direction of rotation of the impression cylinder 502, the respective ink is applied to the substrate as a plurality of ink dots in a desired pattern wherein the combination of all of the ink dots defines the completed graphic 61. Alternatively, or additionally, the raised photopolymer plates of the apparatus 500 can contain solid regions that are raised and are in the shape of the desired object. In such an embodiment the printed image will be solid, as opposed to a plurality of dots, having the desired configuration.

Inks used with the flexographic printing apparatus 500 are suitably low viscosity ink formulations known to those skilled in the art. For example, suitable non-phosphorescent inks (broadly, non-phosphorescent materials) useful with the flexographic printing apparatus 500 to define a non-phosphorescent region 202 on the substrate 506 may be formulated with one or a combination of resins including, but not limited to, acrylics, urethanes, polyamides and nitrocellulose. Suitable solvents for the ink can contain one a combination of alcohols, acetetates, glycol ethers and water. For example, such solvents may comprise about 70–100% alcohol, about 0–30% acetate, and about 0–30% glycol ether.

It is also contemplated that the non-phosphorescent ink may be a fluorescent ink without departing from the scope of this invention. As used herein, the term fluorescent refers to the ability to absorb electromagnetic energy (e.g., light) from a source thereof and subsequently emit electromagnetic energy at a different wavelength than the source while in the presence of the electromagnetic energy source, but not for more than a very short time period following the removal of the electromagnetic energy source.

Phosphorescent ink (broadly, phosphorescent material) suitable for use with the flexographic printing apparatus 500 to define a phosphorescent region 204 on the substrate 506 generally comprises a phosphorescent substance and a solvent blend. For example, one suitable phosphorescent substance is strontium aluminate. Another suitable phosphorescent substance is zinc sulfide. The solvent blend is suitably the same as that described previously as suitable for preparing the non-phosphorescent ink. As an example, one suitable phosphorescent ink is available from Sun Chemical of Fort Lee, N.J., U.S.A. under the designation GlowPac.

The phosphorescent ink is suitably applied to the substrate by the last print cylinder (e.g., print cylinder 508f in FIG. 8) along the direction of movement of the substrate 506 (e.g., in the direction of rotation of the impression cylinder 502) to inhibit contamination of the print cylinders used to apply the non-phosphorescent ink to the substrate. However, it is understood that the phosphorescent ink may instead, or may additionally, be applied to the substrate by any one or more of the other print cylinders 508a, 508b, 508c, 508d, 508e without departing from the scope of this invention.

Figure 5A:
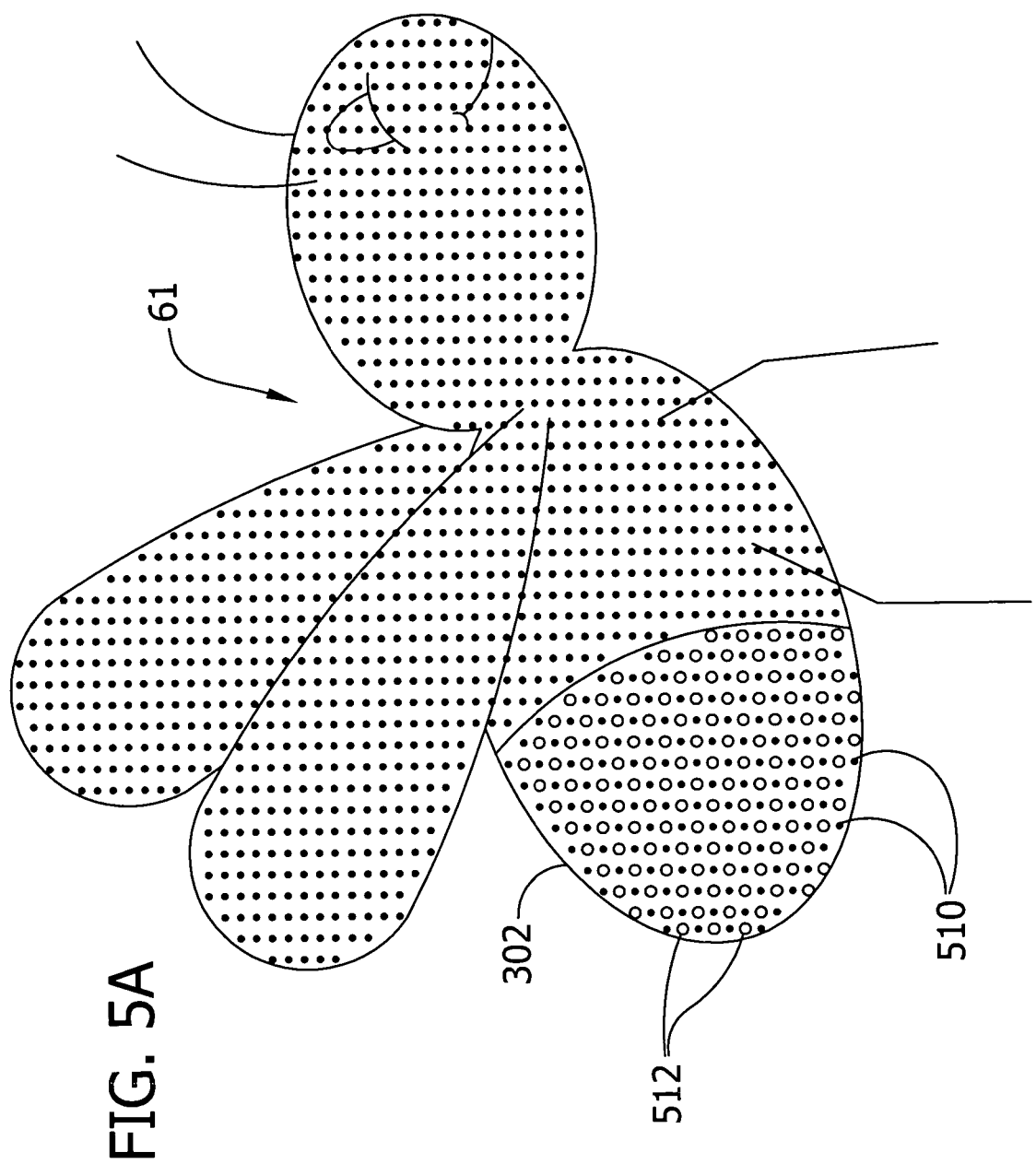
FIG. 5a is an enlarged view of the graphic of FIG. 5.

With particular reference to FIG. 5a, dots 510 of non-phosphorescent ink (shown as solid dots in FIG. 5a) are interspersed with dots 512 of phosphorescent ink (shown as circles in FIG. 5a) to define the overlapping region of the graphic 61. The dots 512 of phosphorescent ink can at least in part contact the dots 510 of non-phosphorescent ink. Alternatively, the dots 512 of phosphorescent ink can be discrete from (e.g., out of contact with) the dots 510 of non-phosphorescent ink as shown in FIG. 5a.

The area concentration of phosphorescent ink within the overlapping region (e.g., the area within the overlapping region that is covered by phosphorescent ink) is suitably in the range of about 1 percent to about 100 percent of the total area of the overlapping region, and more suitably in the range of about 20 percent to about 80 percent. In one particularly suitable embodiment, the area concentration of the phosphorescent ink within the overlapping region is about 50 percent of the total area of the overlapping region. The dots 512 of phosphorescent ink and the dots 510 of non-phosphorescent ink may be of substantially the same size, or they may be of different sizes. It is also contemplated that the density (e.g., dots per unit of area) of the phosphorescent ink dots 512 within the overlapping region may be substantially the same as the density of non-phosphorescent dots 510 therein, or the dot densities may be different.

It is understood that conventional printing techniques other than flexographic printing may used to apply the phosphorescent region 204 and/or the colored non-phosphorescent region 202 to the pants 20 without departing from the scope of this invention. For example, other suitable printing techniques include, without limitation, screen printing, rotogravure printing in which an engraved print roll is utilized, and ink jet printing in which nozzles spray ink droplets that are selectively deflected by an electrostatic charge onto a substrate.

Where a non-phosphorescent material is applied to the substrate in any of the above described embodiments, e.g., to the inner layer of the outer cover 40 of the pants 20, the non-phosphorescent region 202 is suitably visibly distinguishable from the substrate itself, e.g., it is a different shade and/or color than the substrate itself. For example, where the substrate is generally white, the non-phosphorescent material is suitably colored to define a colored non-phosphorescent region 202 of the graphic 61. As used in reference to the non-phosphorescent region, the term "colored" is intended to mean having a color other than white. Alternatively, the substrate (e.g., the material(s) from which the substrate is formed) may be colored upon its initial formation by any technique known in the art, in which case the non-phosphorescent material applied to the substrate is suitably a different color, including white as that term is defined herein, than the substrate, or the phosphorescent material is a sufficiently different shade of the color of the substrate, so as to be visibly distinguishable from the substrate under normal light conditions. The non-phosphorescent material may also, or may instead, be non-transparent so as to define a non-transparent non-phosphorescent region of the graphic 61.

The term "non-transparent" as used here refers to the inability of light to pass through the non-phosphorescent material.

In another embodiment, the substrate may be conventionally colored upon its initial formation as described above to be colored and non-phosphorescent, thereby defining the non-phosphorescent region 202 of the graphic. In such an embodiment, the phosphorescent material is applied to the substrate to define the phosphorescent region 204 of the graphic in overlapping relationship with the colored non-phosphorescent region 202.

Figure 9:
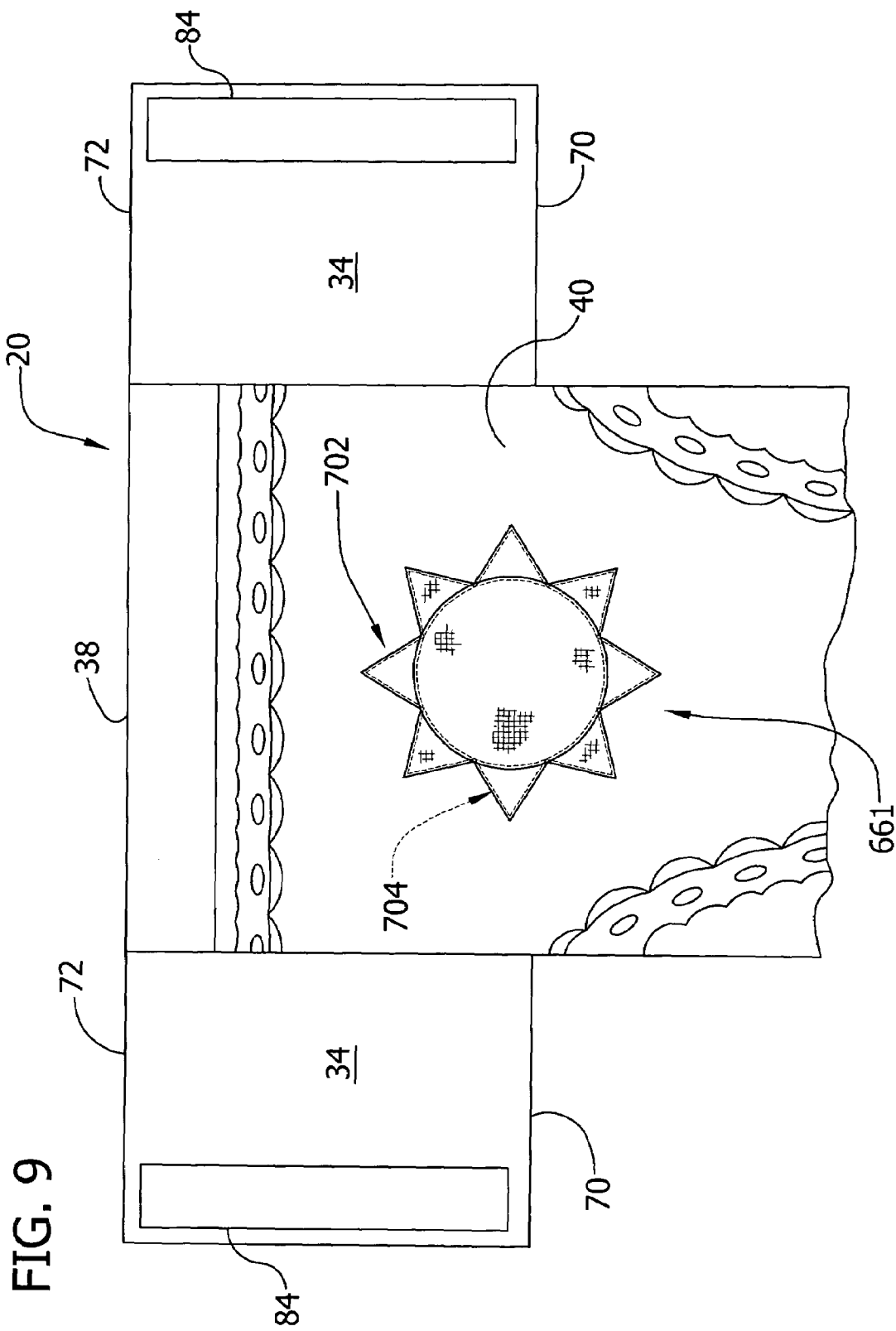
FIG. 9 is a plan view similar to FIG. 2 with a fifth embodiment of a graphic of the present invention applied to the pants.

In another embodiment, which is shown in FIG. 9, the graphic 661 is similar to the graphic 61 of FIG. 4 but with a non-photoluminescent region (shown in solid lines in FIG. 9 and indicated generally at 702) on the outer cover 40, and more particularly the inner layer of the outer cover, of the pants 20 and a photoluminescent region (shown in phantom lines in FIG. 9 and indicated generally at 704) also on the inner layer of the outer cover of the pants. As used herein, the term "photoluminescent" refers to the ability to luminesce as a result of absorbing electromagnetic radiation (e.g., light) from a source thereof and emitting electromagnetic radiation at a different wavelength than the source of electromagnetic radiation. For example phosphorescent materials and fluorescent materials are both photoluminescent. The term "non-photoluminescent" therefore refers to an inability to absorb electromagnetic energy and luminesce in response thereto.

Thus, the non-photoluminescent region 702 of the graphic 661 is generally visible under "normal" light conditions but becomes substantially less visible in low light conditions, and in particular in the absence of light. In contrast, upon exposure of the photoluminescent region to light sufficient to cause luminescence of the photoluminescent region 704, the photoluminescent region luminesces, i.e., emits electromagnetic radiation in low light conditions and/or upon the removal of light so that the photoluminescent region appears brighter or otherwise glows in low light and/or dark conditions.

In the particular embodiment shown in FIG. 9, the non-photoluminescent region 702 of the graphic is in overlapping relationship with the photoluminescent region 704 of the graphic 661, and more particularly it is in registry therewith, to define an overlapping region of the graphic wherein the non-photoluminescent region and the photoluminescent region are in overlapping relationship with each other. Thus, it is to be understood that the phantom lines shown offset from the solid lines in FIG. 9 are for illustrative purposes only. Upon exposure of the overlapping region to light sufficient to cause the photoluminescent region 704 to luminesce, the photoluminescent region luminesces so that the overlapping region appears brighter in low light conditions and/or in the absence of light.

Figure 10:
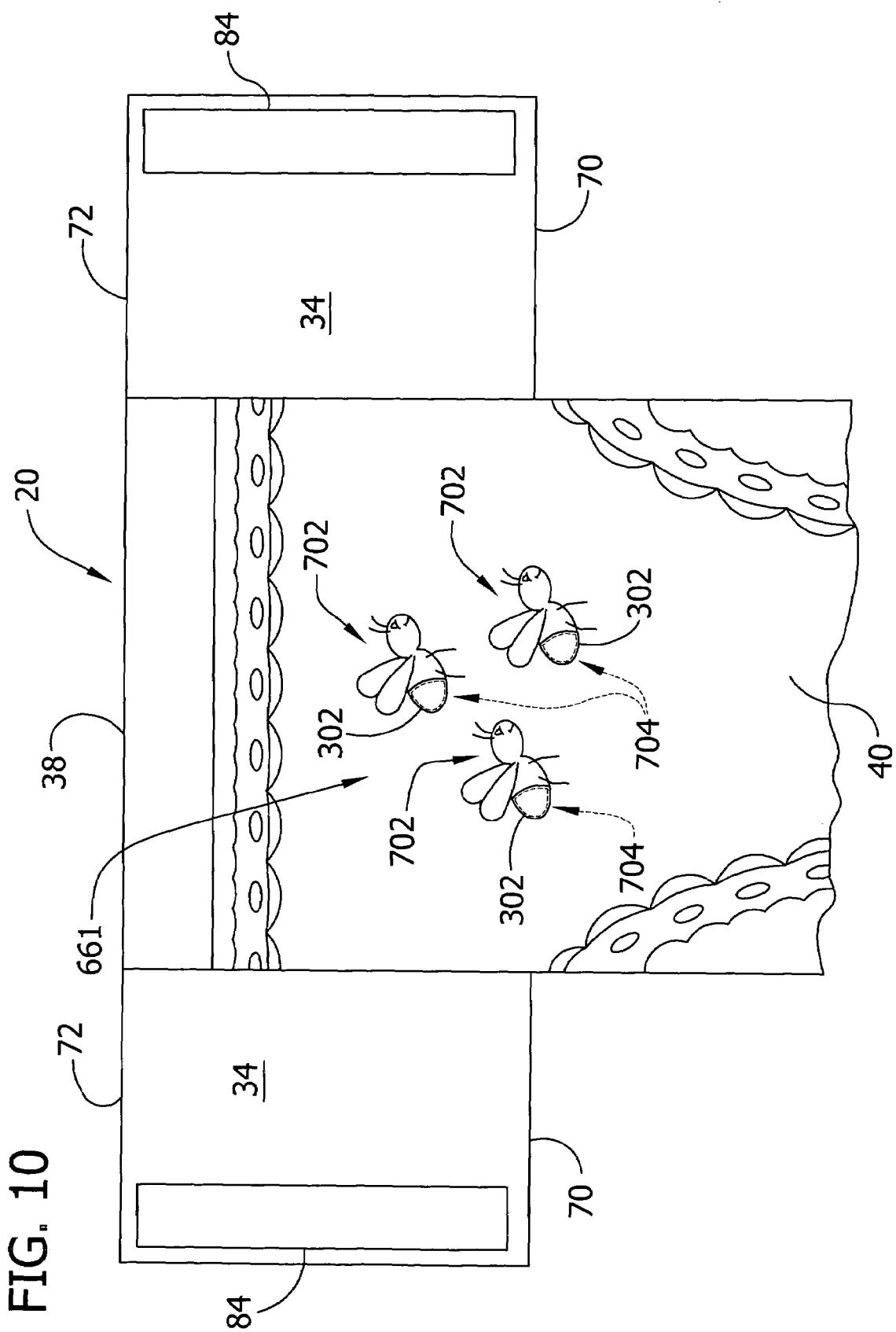
FIG. 10 is a plan view similar to FIG. 2 with a sixth embodiment of a graphic of the present invention applied to the pants.

As shown in FIG. 10, which is similar to FIG. 5, the non-photoluminescent region 702 and the photoluminescent region 704 may be other than in registry with each other as long as at least a portion of the non-photoluminescent region is in overlapping relationship with at least a portion of the photoluminescent region to define an overlapping region of the graphic 661. The overlapping region of the graphic 661 is thus visible in normal light conditions and following exposure to light sufficient to cause the photoluminescent region to luminesce, the portion of the photoluminescent region defining the overlapping region luminesces in low light conditions and/or in the absence of light.

Figure 6:
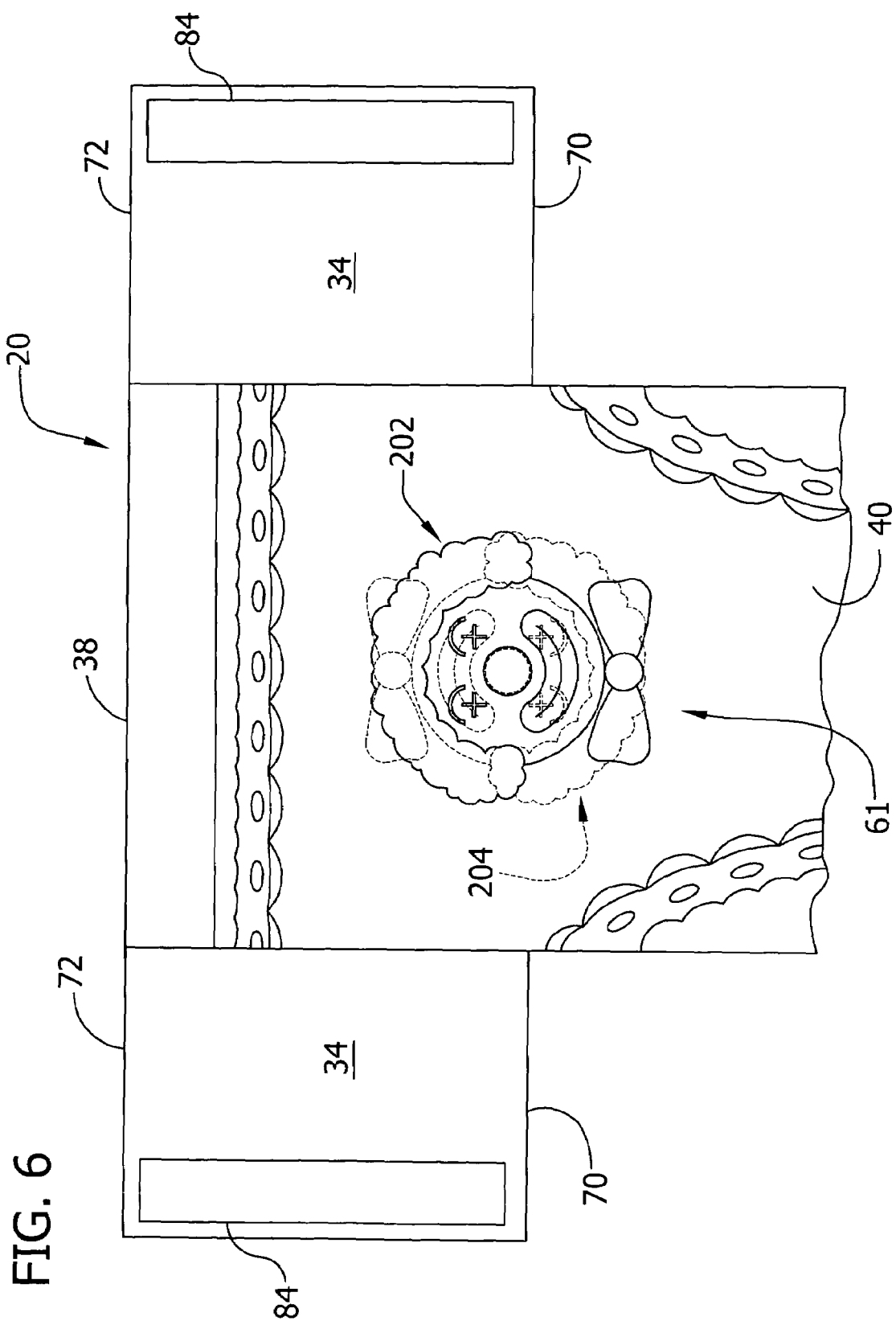
FIG. 6 is a plan view similar to FIG. 2 with a third embodiment of a graphic of the present invention applied to the pants.
Figure 11:
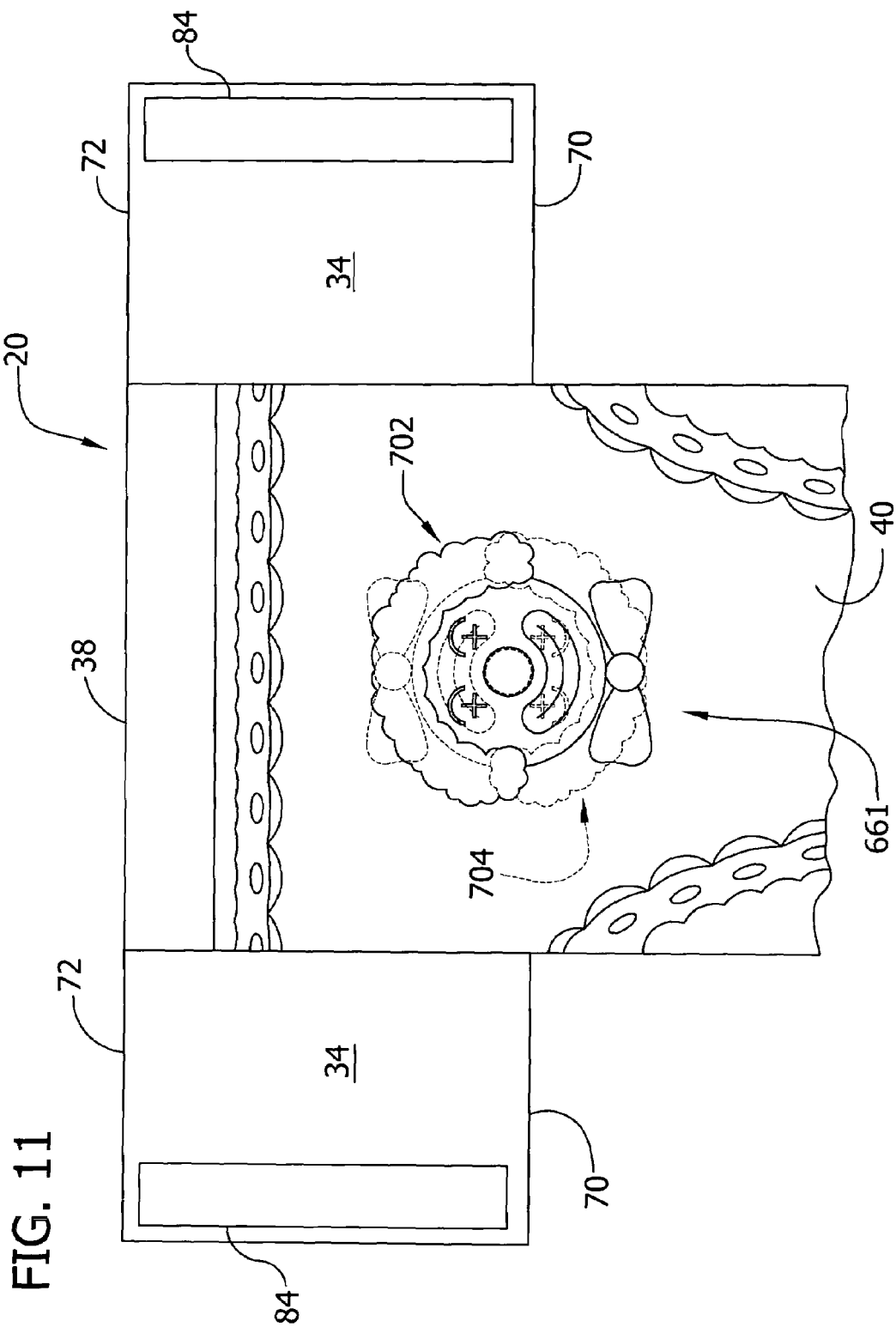
FIG. 11 is a plan view similar to FIG. 2 with a seventh embodiment of a graphic of the present invention applied to the pants.

In the embodiment shown in FIG. 11, which is similar to the embodiment of FIG. 6, the non-photoluminescent region 702 defines a detail of the graphic 661 and the photoluminescent region 704 is a mirror image of the detail. The mirror image detail defined by the photoluminescent region 704 is suitably rotated, such as in the range of about 1 to about 359 degrees, relative to the detail defined by the non-photoluminescent region 702. For example, in the illustrated embodiment the mirror image detail defined by the photoluminescent region 704 is rotated approximately 180 degrees relative to the detail defined by the non-photoluminescent region 702. In such an embodiment, the non-photoluminescent region 702 is visible in normal light conditions. Upon exposure to light sufficient to cause the photoluminescent region to luminesce, the photoluminescent region 704 luminesces while the non-phosphorescent becomes substantially less visible in low light and/or in the absence of light so that the graphic 661 appears rotated (e.g., inverted in the illustrated embodiment) relative to the orientation of the graphic as it appeared in normal light conditions.

In another particular embodiment (FIG. 12, which is similar to FIG. 7), the graphic 661 comprises a non-photoluminescent region 702 (which may be a single color or multiple colors) defining both a background 706 of the graphic as well as one or more details 708 of the graphic. One or more photoluminescent regions 704 of the graphic 661 are disposed entirely within the colored non-photoluminescent region 702 in overlapping relationship, and more particularly in registry, with the details 708 of the graphic. In normal light conditions, the entire background 706 and details 708 of the graphic 661 are visible, while following exposure of the background and details to light sufficient to cause the photoluminescent region to luminesce, the details of the graphic luminesce in low light conditions and/or in the absence of light.

It is also contemplated that the non-photoluminescent region 702 may define only a background (e.g., such as background 706 of FIG. 12) of the graphic 661 and that the photoluminescent region 704 or regions may define details (e.g., such as details 708 of FIG. 12) disposed entirely within the non-photoluminescent region in overlapping relationship therewith. In such an embodiment, the overlapping region or regions are visible in normal light conditions only as the background of the graphic 661 while following exposure to light sufficient to cause the photoluminescent region to luminesce, only the details luminesce in low light conditions and/or in the absence of light.

In yet another particular embodiment, the photoluminescent region 704 may be in overlapping relationship with the non-photoluminescent region 702 throughout all or part of the background of the graphic 661 but be discrete from (e.g., in non-overlapping relationship with) the details of the graphic. In such an embodiment, the entire background and details of the graphic 661 are visible in normal light conditions. In low conditions and/or in the absence of light following exposure to light sufficient to cause the photoluminescent region to luminesce, the background of the graphic 661 luminesces while the details remain substantially un-illuminated so that the details are recognizable against the luminescent background.

It is further contemplated that the background of the graphic 661 described in any of the above embodiments may comprise a vignette, i.e., the background gradually changes shades of color and/or gradually changes in glow intensity from one portion of the background to another.

In one embodiment, the non-photoluminescent region of the graphic 661 is formed by applying a non-photoluminescent material to the outer cover 40 of the pants 20, and more particularly to the inner layer (broadly, a substrate) thereof. Similarly, the photoluminescent region of the graphic 661 is formed by applying a photoluminescent material to the inner layer of the outer cover 40. As used herein in reference to applying the non-photoluminescent and photoluminescent materials to a substrate such as the inner layer of the outer cover 40, the terms "apply," "applying," and "applied" are intended to refer to the respective material being applied to the substrate following initial formation of the substrate, such as by imprinting, adhering, spraying, etc. onto the substrate.

More suitably, both the non-photoluminescent material and the photoluminescent material are applied to the outer face of the inner layer of the outer cover 40. However, it is understood that the non-photoluminescent material may be applied to an inner face of the inner layer of the outer cover 40 while the photoluminescent material is applied to the outer face of the inner layer, or vice versa, as long as portions of the respective regions 702, 704 defined by the applied photoluminescent and non-photoluminescent materials are in overlapping relationship with each other to define an overlapping region of the graphic 661. It is also contemplated that both the non-photoluminescent material and the photoluminescent material may be applied to the inner face of the inner layer of the outer cover 40 and remain within the scope of this invention.

Alternatively, both the photoluminescent material and the non-photoluminescent material may be applied to the nonwoven outer layer (also broadly referred to as a substrate) of the outer cover 40, or one of the photoluminescent material and the non-photoluminescent material may be applied to the outer layer of the outer cover while the other is applied to the inner layer of the outer cover, as long as the inner and outer layers are overlaid relationship with each other so that the respective regions 702, 704 defined by the applied photoluminescent and non-photoluminescent materials are in overlapping relationship with each other. It is also understood that the graphic 661 may be applied to any of the other components of the training pants 20, such as the liner 42, side panels 34, 134, etc., without departing from the scope of this invention.

Both the photoluminescent material and the non-photoluminescent material are suitably applied to the pants 20 by the flexographic printing apparatus 500 as described previously or by other suitable printing techniques. For example, one or more photoluminescent inks may be used to form the photoluminescent region 704 of the graphic 661 and one or more non-photoluminescent inks may be used to form the non-photoluminescent region 702 of the graphic. The non-photoluminescent ink may be one or more of the inks described previously as being non-phosphorescent inks, excluding fluorescent inks. The photoluminescent ink may be a phosphorescent ink such as that described previously, or it may be a fluorescent ink as was also described previously.

The area concentration of photoluminescent ink within the overlapping region (e.g., the area within the overlapping region that is covered by photoluminescent ink) is suitably in the range of about 1 percent to about 100 percent of the total area of the overlapping region, and more suitably in the range of about 20 percent to about 80 percent. In one particularly suitable embodiment, the area concentration of the photoluminescent ink within the overlapping region is about 50 percent of the total area of the overlapping region.

It is understood that conventional printing techniques other than flexographic printing may used to apply the photoluminescent region 704 and/or the colored non-photoluminescent region 702 to the pants 20 without departing from the scope of this invention. For example, other suitable printing techniques include, without limitation, screen printing, rotogravure printing in which an engraved print roll is utilized, and ink jet printing in which nozzles spray ink droplets that are selectively deflected by an electrostatic charge onto a substrate.

Where a non-photoluminescent material is applied to the substrate in any of the above described embodiments, e.g., to the inner layer of the outer cover 40 of the pants 20, the non-photoluminescent material is suitably visibly distinguishable from the substrate itself, e.g., it is a different shade and/or color than the substrate itself. For example, where the substrate is generally white, the non-photoluminescent material is suitably colored to define a colored non-photoluminescent region of the graphic 661. As used in reference to the non-photoluminescent region 702, the term "colored" is intended to mean having a color other than white as described previously. Alternatively, the substrate (e.g., the material(s) from which the substrate is formed) may be colored upon its initial formation by any technique known in the art, in which case the non-photoluminescent material applied to the substrate is suitably a different color, including white as that term is defined herein, than the substrate, or the photoluminescent material is a sufficiently different shade of the color than the substrate, so as to be visibly distinguishable from the substrate under normal light conditions. The non-photoluminescent material may also, or may instead, be non-transparent so as to define a non-transparent non-photoluminescent region 702 of the graphic 661. The term "non-transparent" as used here refers to the inability of light to pass through the non-photoluminescent material.

In another embodiment, the substrate may be conventionally colored upon its initial formation as described above to be colored and non-photoluminescent, thereby defining the non-photoluminescent region 702 of the graphic 661. In such an embodiment, the photoluminescent material is applied to the substrate to define the photoluminescent region 704 of the graphic 661 in overlapping relationship with the colored non-photoluminescent region 702.

Glow Intensity Test

The following Glow Intensity Test can be performed to determine the glow intensity, in terms of lux value, of the overlapping region of a graphic of the present invention, such as on a substrate or an article incorporating the graphic.

Test equipment to be used for the Glow Intensity Test comprises a table having a flat table top of at least about 24 inches by about 24 inches. The table is covered by a black cloth. A pair of flood lamps are positioned approximately 12 inches above opposite sides of the table and are pointed down toward the center of the table generally at an angle of about 45 degrees. The lamps are incandescent Sylvania 150 watt flood lamps. The intensity of the flood lamps is controlled with a suitable voltage regulator to have an illumination of about 2080 lux (9.7 aperture reading) as determined by a flashmeter, such as is commercially available from Minolta as model designation Flashmeter IV, positioned approximately 5 cm above the center of the table top.

An image analysis system available from Carl Zeiss, Inc. of Thornwood, N.Y., U.S.A. under model designation Zeiss KS400 Image Analysis System is used to capture and analyze an image of the sample during testing. The system is equipped with an Axiocam CCD camera (1,300×1,300 pixels full chip, 8 bit gray scale) using 4×4 binning (325× 328 pixels) with a camera gain of 2 for an integration time of 5 seconds. An attached Nikon 20 mm lens (f2.8) provides an approximately 80 mm by 63 mm field of view. The camera is centrally positioned above the table at a height such that the overlapping region of the graphic on the sample comprises in the range of about 10% to about 30% of the 80 mm by 63 mm field of view of the camera.

To conduct the Glow Intensity Test, a sample, such as a substrate or an article, or a cut portion thereof, having a graphic comprising overlapping phosphorescent and non-phosphorescent regions, or overlapping photoluminescent and non-photoluminescent regions, is used. The sample may be of substantially any size as long as it can lie flat on the table top with the overlapping region of the graphic comprising in the range of about 10% to about 30% of the field of view of the camera. This allows sufficient contrast between the glowing region and non-glowing region of the sample within the images captured by the camera.

The sample should be kept in a dark environment (e.g., below flashmeter sensitivity) for a minimum of five minutes prior to conducting the test. The sample is then laid flat on the table. If necessary to maintain the sample flat, a ⅛ inch glass plate sized larger than the portion of the sample within the field of view may be placed over the viewed portion of the sample. The flood lamps are then turned on so that the sample is exposed to the incident light from the lamps for a period of 10 minutes. The lux level of the flood lamp illumination should be determined using the flashmeter.

After the 10 minute period of exposure, the flood lamps are turned off and allowed to power down for a period of about 0.5 seconds. A timer is then started and data acquisition is intiated with a first image of the viewed portion of the sample being captured by the image analysis system at 0.01 seconds. A binary mask is created from the first image, using the KS400 system automatic contrast enhancement, delineation (size: 10, thr: 3) and thresholding to discriminate the glowing portion of the image (e.g., the overlapping region of the graphic) from the non-glowing portion of the image. Pixels at ≧50% of the light intensity of the brightest pixel in the image were classified as glowing, while all other pixels were classified as non-glowing and were masked. The mask is also used in processing all subsequent images captured of the sample being tested. Additional images are captured and analyzed every 10 seconds up to 280 seconds. Each image is captured over a five second period.

For each captured image, the mean glow intensity for the glowing region of the image and the mean glow intensity for the non-glowing region are calculated. To mean glow intensity of the sample is then adjusted by substracting the mean glow intensity determined for the non-glowing region from the mean glow intensity determined for the glowing region (otherwise referred to as determining the glow intensity difference). With appropriate calibration of the camera using standard illuminants, as is known in the art, the calculated glow intensities can be converted to lux values.

Experiment

Figure 13A:
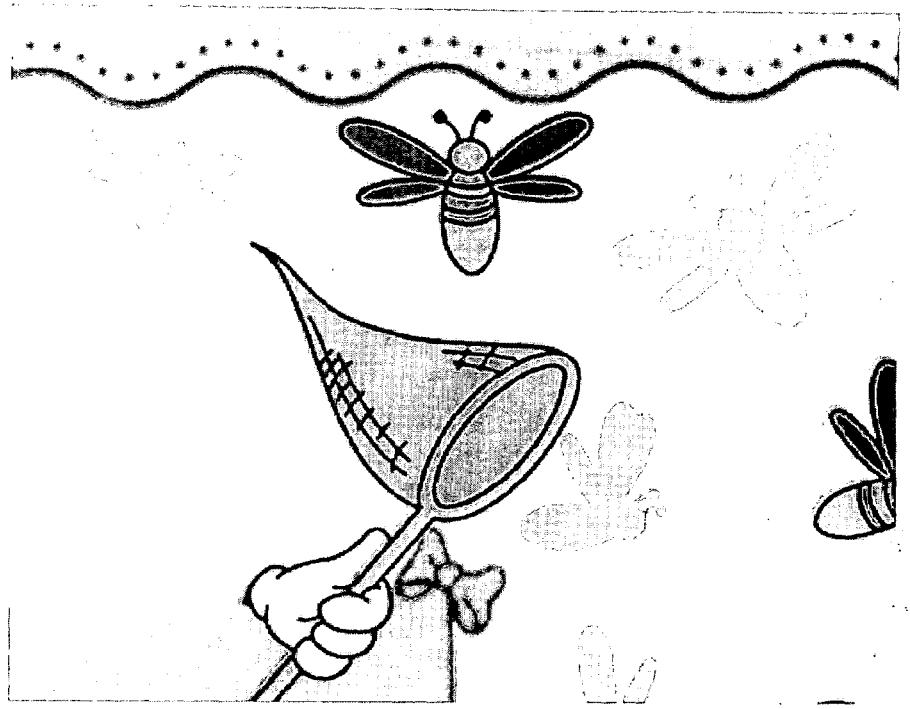
FIG. 13a is an image captured during a Glow Intensity Test with the test sample illuminated.
Figure 13B:
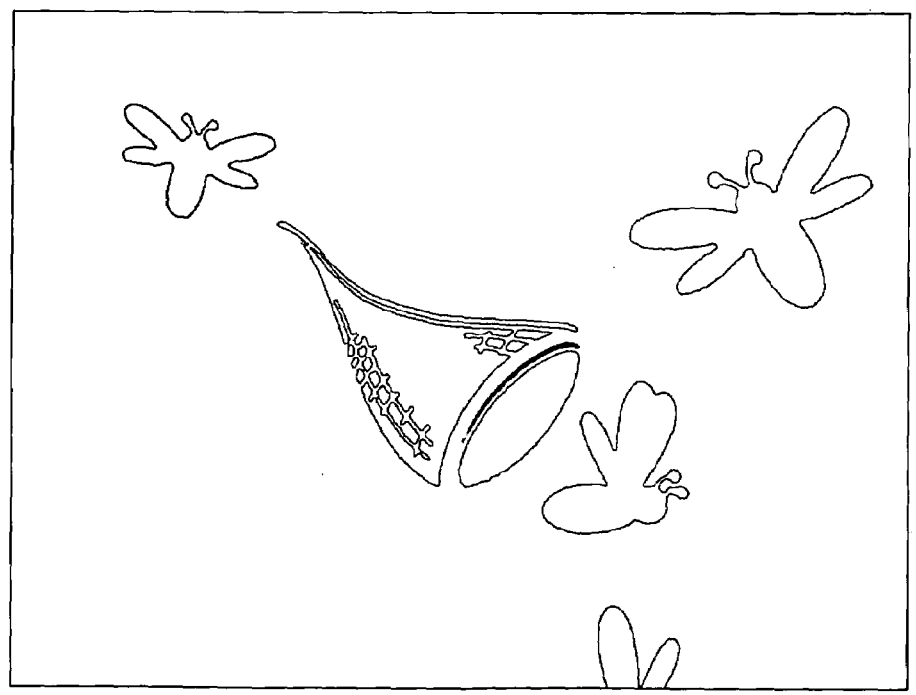
FIG. 13b is another image captured during a Glow Intensity with the test sample shown in the dark and having glowing regions within the image.

A polyethylene film measuring approximately 3 ft. by 5 inches and having graphics such as shown in FIG. 13a and constructed in accordance with the present invention was subjected to the Glow Intensity Test described previously. The graphics included overlapping photoluminescent and non-photoluminescent regions such as the butterfly net and non-outlined fireflies shown in FIG. 13a, which were colored yellow with non-photoluminescent ink. The overlapping regions were formed by equal concentrations of photoluminescent and non-photoluminescent inks as described previously herein. FIG. 13b illustrates the glowing overlapping region within the image captured by the camera during testing.

The following table sets forth the mean glow intensity (i.e., the mean glow intensity of the glowing region within the image minus the mean glow intensity of the non-glowing region within the image), as a lux value, determined for the images captured at each time period following power down of the flood lamps during the Glow Intensity Test.

| Time (sec) | Mean Glow Intensity (lux) |
|---|---|
| 0.01 | 1.47 |
| 10 | 1.02 |
| 20 | 0.83 |
| 30 | 0.71 |
| 40 | 0.62 |
| 50 | 0.56 |
| 60 | 0.50 |
| 70 | 0.46 |
| 80 | 0.43 |
| 90 | 0.40 |
| 100 | 0.37 |
| 110 | 0.35 |
| 120 | 0.33 |
| 130 | 0.31 |
| 140 | 0.29 |
| 150 | 0.28 |
| 160 | 0.27 |
| 170 | 0.25 |
| 180 | 0.24 |
| 190 | 0.23 |
| 200 | 0.22 |
| 210 | 0.21 |
| 220 | 0.21 |
| 230 | 0.20 |
| 240 | 0.19 |
| 250 | 0.19 |
| 260 | 0.18 |
| 270 | 0.17 |
| 280 | 0.17 |

It is understood that where a non-woven web is laminated over the tested film, such as in the manner of the outer cover 40 of the training pants 20 described herein, the glow intensity may be less than that set forth in the above table depending on the construction of the non-woven web.

In one embodiment, the mean glow intensity of the overlapping region of the graphic as determined by the Glow Intensity Test after 60 seconds is suitably at least about 0.15 lux, more suitably at least about 0.25 lux, still more suitably at least about 0.4 lux and most suitably at least about 0.5 lux.

As various changes could be made in the above constructions and methods, without departing from the scope of the invention, it is intended that all matter contained in the above description and shown in the accompanying drawings shall be interpreted as illustrative and not in a limiting sense.

When introducing elements of the invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

What is claimed is:

1. An absorbent article comprising a liner, an outer cover and an absorbent body disposed between the liner and the outer cover, the outer cover at least in part comprising a substrate having a graphic thereon, said graphic comprising a non-phosphorescent ink applied to the substrate to define a non-phosphorescent region of said graphic and a phosphorescent ink applied to the substrate to define a phosphorescent region of said graphic, at least a portion of the non-phosphorescent region and at least a portion of the phosphorescent region being in overlapping relationship with each other so as to define an overlapping region of said graphic wherein when the overlapping region is exposed to light sufficient to cause phosphorescence of the phosphorescent region said at least a portion of the phosphorescent region phosphoresces to render said overlapping region visible in the absence of light, said non-phosphorescent region comprising a plurality of discrete dots of the non-phosphorescent ink applied to the substrate, said phosphorescent region comprising a plurality of discrete dots of the phosphorescent ink applied to the substrate, the discrete dots of phosphorescent ink being interspersed with the discrete dots of non-phosphorescent ink in the overlapping region of the graphic.

2. The absorbent article set forth in claim 1 wherein the non-phosphorescent region of the graphic is in registry with the phosphorescent region thereof.

3. The absorbent article set forth in claim 1 wherein an area concentration of phosphorescent ink in the overlapping region is in the range of about 20 percent to about 80 percent of the area of the overlapping region.

4. The absorbent article set forth in claim 3 wherein the area concentration of phosphorescent ink in the overlapping region is about 50 percent of the area of the overlapping region.

5. The absorbent article set forth in claim 1 wherein the non-phosphorescent ink is a fluorescent ink.

6. The absorbent article set forth in claim 1 wherein the non-phosphorescent region comprises at least two non-phosphorescent inks applied to said substrate.

7. The absorbent article set forth in claim 6 wherein at least one of the non-phosphorescent inks is fluorescent.

8. The absorbent article set forth in claim 1 wherein the substrate has an inner face and an outer face, one of the non-phosphorescent ink and the phosphorescent ink being applied to the inner face of the substrate and the other one of the non-phosphorescent ink and the phosphorescent ink being applied to the outer face of the substrate.

9. The absorbent article set forth in claim 1 wherein the non-phosphorescent region defines a background of the graphic, the phosphorescent region being disposed substantially within the non-phosphorescent region in overlapping relationship therewith whereby the overlapping region defines a detail of the graphic.

10. The absorbent article set forth in claim 9 wherein the background defined by the non-phosphorescent region is a vignette.

11. The absorbent article set forth in claim 1 wherein the non-phosphorescent region comprises a background and at least one detail within the background, the phosphorescent region being in overlapping relationship with the non-phosphorescent region within the background, said detail defined by the non-phosphorescent region being discrete from said phosphorescent region.

12. The absorbent article set forth in claim 1 wherein the non-phosphorescent region defines a detail of the graphic, the phosphorescent region defining a detail that is a mirror image of the detail defined by the non-phosphorescent region and is in at least partially overlapping relationship with the detail defined by the non-phosphorescent region, the detail defined by the phosphorescent region being rotated relative to the detail defined by the non-phosphorescent region.

13. The absorbent article set forth in claim 1 wherein the substrate is a film.

14. The absorbent article set forth in claim 1 wherein the substrate is a non-woven web.

15. The absorbent article set forth in claim 1 wherein the non-phosphorescent ink is a colored non-phosphorescent ink.

16. The absorbent article set forth in claim 1 wherein the non-phosphorescent region is non-transparent.

17. The absorbent article set forth in claim 1 wherein the non-phosphorescent region is visibly distinguishable from the substrate under normal light conditions.

18. The absorbent article set forth in claim 1 wherein the graphic has a glow intensity as determined by a Glow Intensity Test at 60 seconds of at least about 0.15 lux.

19. The absorbent article set forth in claim 18 wherein the graphic has a glow intensity as determined by a Glow Intensity Test at 60 seconds of at least about 0.5 lux.

20. An absorbent article comprising a liner, an outer cover and an absorbent body disposed between the liner and the outer cover, the outer cover at least in part comprising a substrate having a graphic thereon, said graphic comprising a colored non-phosphorescent region and a phosphorescent region, at least a portion of the non-phosphorescent region and at least a portion of the phosphorescent region being in overlapping relationship with each other so as to define an overlapping region of said graphic wherein when the overlapping region is exposed to light sufficient to cause phosphorescence of the phosphorescent region said at least a portion of the phosphorescent region phosphoresces to render said overlapping region visible in the absence of light, the non-phosphorescent region being defined by a plurality of discrete dots of a non-phosphorescent ink being applied to the substrate, the phosphorescent region being defined by a plurality of discrete dots of a phosphorescent ink applied to the substrate, the discrete dots of phosphorescent ink being interspersed with the discrete dots of non-phosphorescent ink in the overlapping region of the graphic.

21. The absorbent article set forth in claim 20 wherein at least a portion of the substrate is colored to define said colored non-phosphorescent region.

22. An absorbent article comprising a liner, an outer cover and an absorbent body disposed between the liner and the outer cover, the outer cover at least in part comprising a first substrate, a second substrate in overlaid relationship with the first substrate, and a graphic comprising a colored non-phosphorescent region and a phosphorescent region, at least a portion of the colored non-phosphorescent region and at least a portion of the phosphorescent region being in overlapping relationship with each other so as to define an overlapping region of said graphic wherein when said overlapping region is exposed to light sufficient to cause phosphorescence of the phosphorescent region, said at least a portion of the phosphorescent region phosphoresces to render said overlapping region visible in the absence of light, one of said first and second substrates having the colored non-phosphorescent region thereon and the other one of said first and second substrates having the phosphorescent region thereon, the non-phosphorescent region being defined by a plurality of discrete dots of a non-phosphorescent ink applied to one of said first and second substrates, the phosphorescent region being defined by a plurality of discrete dots of a phosphorescent ink applied to the other one of said first and second substrates, the discrete dots of phosphorescent ink being interspersed with the discrete dots of non-phosphorescent ink in the overlapping region of the graphic.

23. The absorbent article set forth in claim 22 wherein the graphic has a glow intensity as determined by a Glow Intensity Test at 60 seconds of at least about 0.15 lux.

24. The absorbent article set forth in claim 23 wherein the graphic has a glow intensity as determined by a Glow Intensity Test at 60 seconds of at least about 0.5 lux.

25. An absorbent article comprising a liner, an outer cover and an absorbent body disposed between the liner and the outer cover, the outer cover at least in part comprising a substrate having a graphic thereon, said graphic comprising a non-photoluminescent ink applied to the substrate to define a non-photoluminescent region of said graphic and a photoluminescent ink applied to the substrate to define a photoluminescent region of said graphic, at least a portion of the non-photoluminescent region and at least a portion of the photoluminescent region being in overlapping relationship with each other so as to define an overlapping region of said graphic wherein when the overlapping region is exposed to light sufficient to cause luminescence of the photoluminescent region said at least a portion of the photoluminescent region luminesces, said non-photoluminescent region comprising a plurality of discrete dots of the non-photoluminescent ink applied to the substrate, said photoluminescent region comprising a plurality of discrete dots of the photoluminescent ink applied to the substrate, the discrete dots of photoluminescent ink being interspersed with the discrete dots of non-photoluminescent ink in the overlapping region of the graphic.

26. The absorbent article set forth in claim 25 wherein the non-photoluminescent region of the graphic is in registry with the photoluminescent region thereof.

27. The absorbent article set forth in claim 25 wherein an area concentration of photoluminescent ink in the overlapping region is in the range of about 20 percent to about 80 percent of the area of the overlapping region.

28. The absorbent article set forth in claim 27 wherein the area concentration of photoluminescent ink in the overlapping region is about 50 percent of the area of the overlapping region.

29. The absorbent article set forth in claim 25 wherein the photoluminescent ink is at least one of phosphorescent and fluorescent.

30. The absorbent article set forth in claim 25 wherein the non-photoluminescent region comprises at least two non-photoluminescent inks applied to said substrate.

31. The absorbent article set forth in claim 25 wherein the substrate has an inner face and an outer face, one of the non-photoluminescent ink and the photoluminescent ink being applied to the inner face of the substrate and the other one of the non-photoluminescent ink and the photoluminescent ink being applied to the outer face of the substrate.

32. The absorbent article set forth in claim 25 wherein the non-photoluminescent region defines a background of the graphic, the photoluminescent region being disposed substantially within the non-photoluminescent region in overlapping relationship therewith whereby the overlapping region defines a detail of the graphic.

33. The absorbent article set forth in claim 32 wherein the background defined by the non-photoluminescent region is a vignette.

34. The absorbent article set forth in claim 25 wherein the non-photoluminescent region comprises a background and at least one detail within the background, the photoluminescent region being in overlapping relationship with the non-photoluminescent region within the background, said detail defined by the non-photoluminescent region being discrete from said photoluminescent region.

35. The abosorbent article as set forth in claim 25 wherein the non-photoluminescent region defines a detail of the graphic, the photoluminescent region defining a detail that is a mirror image of the detail defined by the non-photoluminescent region and is in at least partially overlapping relationship with the detail defined by the non-photoluminescent region, the detail defined by the photoluminescent region being rotated relative to the detail defined by the non-photoluminescent region.

36. The absorbent article set forth in claim 25 wherein the substrate is a film.

37. The absorbent article set forth in claim 25 wherein the substrate is a non-woven web.

38. The absorbent article set forth in claim 25 wherein the non-photoluminescent ink is a colored non-photoluminescent material.

39. The absorbent article set forth in claim 25 wherein the non-photoluminescent region is non-transparent.

40. The absorbent article set forth in claim 25 wherein the non-photoluminescent region is visibly distinguishable from the substrate under normal light conditions.

41. The absorbent article set forth in claim 25 wherein the graphic has a glow intensity as determined by a Glow Intensity Test at 60 seconds of at least about 0.15 lux.

42. The absorbent article set forth in claim 41 wherein the graphic has a glow intensity as determined by the Glow Intensity Test at 60 seconds of at least about 0.5 lux.

43. An absorbent article comprising a liner, an outer cover and an absorbent body disposed between the liner and the outer cover, the outer cover at least in part comprising a substrate having a graphic thereon, said graphic comprising a colored non-photoluminescent region and a photoluminescent region, at least a portion of the non-photoluminescent region and at least a portion of the photoluminescent region being in overlapping relationship with each other so as to define an overlapping region of said graphic wherein when the overlapping region is exposed to light sufficient to cause luminescence of the photoluminescent region said at least a portion of the photoluminescent region luminesces, the non-photoluminescent region being defined by a plurality of discrete dots of a non-photoluminescent ink being applied to the substrate, the photoluminescent region being defined by a plurality of discrete dots of a photoluminescent ink applied to the substrate, the discrete dots of photoluminescent ink being interspersed with the discrete dots of non-photoluminescent ink in the overlapping region of the graphic.

44. The absorbent article set forth in claim 43 wherein at least a portion of the substrate is colored to define said colored non-photoluminescent region.

45. An absorbent article comprising a liner, an outer cover and an absorbent body disposed between the liner and the outer cover, the outer cover at least in part comprising a first substrate, a second substrate in overlaid relationship with the first substrate, and a graphic comprising a colored non-photoluminescent region and a photoluminescent region, at least a portion of the colored non-photoluminescent region and at least a portion of the photoluminescent region being in overlapping relationship with each other so as to define an overlapping region of said graphic wherein when said overlapping region is exposed to light sufficient to cause luminescence of the photoluminescent region, said portion of the photoluminescent region luminesces, one of said first and second substrates having the colored non-photoluminescent region thereon and the other one of said first and second substrates having the photoluminescent region thereon, the non-photoluminescent region being defined by a plurality of discrete dots of a non-photoluminescent ink being applied to one of said first and second substrates, the photoluminescent region being defined by a plurality of discrete dots of a photoluminescent ink applied to other one of said first and second substrates, the discrete dots of photoluminescent ink being interspersed with the discrete dots of non-photoluminescent ink in the overlapping region of the graphic.

46. The absorbent article set forth in claim 45 wherein the graphic has a glow intensity as determined by a Glow Intensity Test at 60 seconds of at least about 0.15 lux.

47. The absorbent article set forth in claim 46 wherein the graphic has a glow intensity as determined by a Glow Intensity Test at 60 seconds of at least about 0.5 lux.

* * * * *